(12) United States Patent
Lowery

(10) Patent No.: US 12,343,173 B2
(45) Date of Patent: *Jul. 1, 2025

(54) SYSTEMS AND METHODS FOR OBTAINING CARDIOVASCULAR PARAMETERS

(71) Applicant: Covidien LP, Mansfield, MA (US)

(72) Inventor: Guy Russell Lowery, San Juan Capistrano, CA (US)

(73) Assignee: Covidien LP, Mansfield, MA (US)

( * ) Notice: Subject to any disclaimer, the term of this patent is extended or adjusted under 35 U.S.C. 154(b) by 767 days.

This patent is subject to a terminal disclaimer.

(21) Appl. No.: 17/479,242

(22) Filed: Sep. 20, 2021

(65) Prior Publication Data
US 2022/0000425 A1    Jan. 6, 2022

Related U.S. Application Data

(63) Continuation of application No. 15/433,935, filed on Feb. 15, 2017, now Pat. No. 11,147,515.
(Continued)

(51) Int. Cl.
*A61B 5/00*    (2006.01)
*A61B 5/0205*  (2006.01)
(Continued)

(52) U.S. Cl.
CPC .......... *A61B 5/6853* (2013.01); *A61B 5/0205* (2013.01); *A61B 5/0261* (2013.01);
(Continued)

(58) Field of Classification Search
CPC ... A61B 5/6853; A61B 5/0205; A61B 5/0261; A61B 5/029; A61B 5/0295; A61B 5/1459; A61B 5/283
See application file for complete search history.

(56) References Cited

U.S. PATENT DOCUMENTS 4,304,239 A    12/1981  Perlin
4,383,534 A     5/1983  Peters
(Continued)

FOREIGN PATENT DOCUMENTS

CN    202236730    5/2012
GB    1467344 A    3/1977
(Continued)

OTHER PUBLICATIONS

"Cardiac Output from an Endotracheal Tube. What Could be Easier?" CONMED Corporation brochure. Sep. 2008.
(Continued)

*Primary Examiner* — May A Abouelela
*Assistant Examiner* — Yasmeen S Warsi

(57) ABSTRACT

A system for measuring cardiovascular data includes an elongate member having a channel, a first expandable member carried by the elongate member and movable between a collapsed state and an expanded state by adjustment initiated externally of a subject, a first sensor disposed on a surface of the elongate member, second and third sensors disposed on a surface of the first expandable, a first optical sensor located at a first location in relation to the distal end of the elongate member and configured for obtaining photoplethysmographic data, and wherein the first expandable member in its expanded state is configured to interface with the subject's larynx for delivery of at least oxygen gas into the respiratory system of the subject, and the second and third sensors are configured to contact tissue in proximity to the larynx when the first expandable member is in its expanded state.

20 Claims, 16 Drawing Sheets

Related U.S. Application Data

(60) Provisional application No. 62/321,525, filed on Apr. 12, 2016, provisional application No. 62/296,069, filed on Feb. 16, 2016.

(51) Int. Cl.

| | |
|---|---|
| *A61B 5/026* | (2006.01) |
| *A61B 5/029* | (2006.01) |
| *A61B 5/0295* | (2006.01) |
| *A61B 5/1455* | (2006.01) |
| *A61B 5/1459* | (2006.01) |
| *A61B 5/283* | (2021.01) |
| *A61J 15/00* | (2006.01) |
| *A61M 16/00* | (2006.01) |
| *A61M 16/04* | (2006.01) |
| *A61B 5/022* | (2006.01) |
| *A61B 5/024* | (2006.01) |
| *A61B 5/08* | (2006.01) |

(52) U.S. Cl.
CPC ............ *A61B 5/029* (2013.01); *A61B 5/0295* (2013.01); *A61B 5/14551* (2013.01); *A61B 5/14552* (2013.01); *A61B 5/1459* (2013.01); *A61B 5/283* (2021.01); *A61B 5/4839* (2013.01); *A61B 5/6857* (2013.01); *A61B 5/6886* (2013.01); *A61J 15/00* (2013.01); *A61J 15/0084* (2015.05); *A61M 16/0069* (2014.02); *A61M 16/021* (2017.08); *A61M 16/0434* (2013.01); *A61M 16/044* (2013.01); *A61M 16/0447* (2014.02); *A61M 16/0461* (2013.01); *A61B 5/02241* (2013.01); *A61B 5/02416* (2013.01); *A61B 5/02427* (2013.01); *A61B 5/026* (2013.01); *A61B 5/08* (2013.01); *A61B 5/7225* (2013.01); *A61B 2562/0209* (2013.01); *A61B 2562/0233* (2013.01); *A61B 2562/06* (2013.01); *A61M 16/0409* (2014.02); *A61M 2202/0208* (2013.01); *A61M 2205/0266* (2013.01); *A61M 2205/3303* (2013.01); *A61M 2205/3306* (2013.01); *A61M 2205/3317* (2013.01); *A61M 2230/06* (2013.01); *A61M 2230/205* (2013.01); *A61M 2230/30* (2013.01); *A61M 2230/50* (2013.01); *A61M 2230/65* (2013.01)

(56) References Cited

U.S. PATENT DOCUMENTS

| | | | |
|---|---|---|---|
| 4,509,514 A | 4/1985 | Brain | |
| 4,640,298 A | 2/1987 | Pless et al. | |
| 4,706,688 A | 11/1987 | Don Michael et al. | |
| 4,817,611 A | 4/1989 | Arzbaecher et al. | |
| 4,836,214 A | 6/1989 | Sramek | |
| 4,852,580 A | 8/1989 | Wood | |
| 5,005,573 A | 4/1991 | Buchanan | |
| 5,010,888 A | 4/1991 | Jadvar et al. | |
| 5,024,228 A | 6/1991 | Goldstone et al. | |
| 5,056,532 A | 10/1991 | Hull et al. | |
| 5,069,215 A | 12/1991 | Jadvar et al. | |
| 5,099,842 A | 3/1992 | Mannheimer et al. | |
| 5,343,860 A | 9/1994 | Metzger et al. | |
| 5,379,765 A | 1/1995 | Kajiwara et al. | |
| 5,584,290 A | 12/1996 | Brain | |
| 5,602,880 A | 11/1997 | Brain | |
| 5,782,774 A | 7/1998 | Shmulewitz | |
| 5,791,349 A | 8/1998 | Shmulewitz | |
| 5,850,832 A | 12/1998 | Chu | |
| 6,095,987 A | 8/2000 | Shmulewitz et al. | |
| 6,292,689 B1 | 9/2001 | Wallace et al. | |
| 6,517,492 B2 | 2/2003 | Koblanski | |
| 7,044,918 B2 | 5/2006 | Diab | |
| 7,220,230 B2 | 5/2007 | Roteliuk et al. | |
| 7,273,053 B2 | 9/2007 | Zocca et al. | |
| 7,422,562 B2 | 9/2008 | Hatib et al. | |
| 8,048,040 B2 | 11/2011 | Kiani | |
| 8,273,053 B2 | 9/2012 | Saltzstein | |
| 8,607,795 B2 | 12/2013 | Cuevas et al. | |
| 8,634,894 B2 | 1/2014 | Rea et al. | |
| 8,721,556 B2 | 5/2014 | Roteliuk | |
| 8,771,197 B2 | 7/2014 | Hatib et al. | |
| 8,801,618 B2 | 8/2014 | Hatib et al. | |
| 8,905,939 B2 | 12/2014 | Hatib et al. | |
| 9,037,226 B2 | 5/2015 | Hacker et al. | |
| 9,289,141 B2 | 3/2016 | Lowery et al. | |
| 9,486,145 B2 | 11/2016 | Feer et al. | |
| 2003/0167010 A1 | 9/2003 | Pinsky | |
| 2003/0167012 A1 | 9/2003 | Friedman et al. | |
| 2003/0176816 A1 | 9/2003 | Maguire et al. | |
| 2005/0065586 A1 | 3/2005 | Johnson | |
| 2005/0066975 A1 | 3/2005 | Brain | |
| 2005/0137647 A1 | 6/2005 | Wallace et al. | |
| 2006/0124132 A1 | 6/2006 | Brain | |
| 2006/0162730 A1 | 7/2006 | Glassenberg et al. | |
| 2007/0000494 A1 | 1/2007 | Banner et al. | |
| 2008/0045813 A1 | 2/2008 | Phuah et al. | |
| 2009/0192381 A1 | 7/2009 | Brockway et al. | |
| 2009/0227885 A1 | 9/2009 | Lowery et al. | |
| 2012/0215074 A1 | 8/2012 | Krimsky | |
| 2013/0146056 A1 | 6/2013 | Baker, Jr. et al. | |
| 2013/0338480 A1 | 12/2013 | Hann | |
| 2014/0073962 A1 | 3/2014 | Addison et al. | |
| 2014/0357956 A1 | 12/2014 | Salahieh et al. | |
| 2015/0112172 A1 | 4/2015 | Atlee et al. | |
| 2015/0173773 A1 | 6/2015 | Bowman et al. | |
| 2016/0345857 A1 | 12/2016 | Jensrud et al. | |
| 2018/0014792 A1 | 1/2018 | Kawabe et al. | |

FOREIGN PATENT DOCUMENTS

| | | |
|---|---|---|
| JP | H06-38937 A | 2/1994 |
| WO | WO 2016179563 | 11/2016 |

OTHER PUBLICATIONS

"Stroke vol. Variation. 'Can We Use Fluid to Improve Hemodynamics?'" Edwards Lifesciences brochure. 2007.

Berkenstadt, H., Margalit, N., Hadani, M., Friedman, Z., Segal, E., Villa, Y., Perel, A., "Stroke Volume Variation as a Predictor of Fluid Responsiveness in Patients Undergoing Brain Surgery," Anesthesia and Analgesia, 2001, pp. 984-989, vol. 92, Williams & Wilkins, Baltimore, USA.

Clearsight System. Edwards Lifesciences brochure. 2014.

Magder, S., "Clinical Usefulness of Respiratory Variations in Arterial Pressure," Americna Journal of Respiratory and Critical Care Medicine, 2004, pp. 151-155, vol. 169, American Lung Association, New York, USA.

Mehta, Y., Arora, D., "Newer methods of cardiac output monitoring," World Journal of Cardiology, Sep. 26, 2014, pp. 1022-1029, vol. 6, No. 9, Baishideng Publishing Group Inc, Pleasanton, USA.

PCT International Search Report and Written Opinion for PCT/US2017/018036, ECOM Medical, Inc., Forms PCT/ISA/220, 210, and 237 dated Jun. 29, 2015 (29 pages).

Mohiaddin, R., Kilner, P., Rees, S., Longmore, D., "Magnetic Resonance vol. Flow and Jet Velocity Mapping in Aortic Coarctation" Journal of the American College of Cardiology 22(5): 1515-1521 (1993).

Uematsu, S., Yang, A., Preziosi, T., Kouba, R., Toung, T., "Measurement of Carotid Blood Flow in Man and its Clinical Application." Stroke 14(2): 256-266 (1983).

Reuter, D., Felbinger, T., Schmidt, C., Kilger, E., Goedje, O., Lamm, P., Goetz, A., "Stroke volume variations for assessment of cardiac responsiveness to volume loading in mechanically ventilated patients after cardiac surgery," Intensive Care Medicine, 2002, pp. 392-398, vol. 28, Springer-Verlag, Berlin, Germany.

SYSTEMS AND METHODS FOR OBTAINING CARDIOVASCULAR PARAMETERS

INCORPORATION BY REFERENCE TO ANY PRIORITY APPLICATIONS

This application is a continuation of U.S. patent application Ser. No. 15/433,935, filed on Feb. 15, 2017, now U.S. Pat. No. 11,147,515, which claims the benefit of priority to U.S. Provisional Patent Application No. 62/296,069, filed on Feb. 16, 2016, and U.S. Provisional Patent Application No. 62/321,525, filed on Apr. 12, 2016, all of which are hereby incorporated by reference in their entirety for all purposes. Priority is claimed pursuant to 35 U.S.C. § 120 and 35 U.S.C. § 119.

FIELD OF THE INVENTION

The field of the invention generally relates to systems for obtaining cardiovascular parameters, at least partially from naturally-occurring internal body surfaces.

BACKGROUND

Physiological monitoring is performed on patients in a variety of settings including, but not limited to, operating rooms/theaters/suites, intensive care units, neurointensive care units, critical care units, surgical wards, neonatal care units, general wards, and home care sites. Cardiovascular monitoring is performed on certain patients within these settings and commonly includes both cardiac monitoring and hemodynamic monitoring. Stroke volume (SV), cardiac output (CO), heart rate (HR), are often measured, estimated, or calculated from data obtained during cardiovascular monitoring. The following equation relates these parameters:

CO=SV×HR (units of volume per time)

Patients in these settings are monitored, as well as manipulated, in order to allow and maintain optimal delivery of oxygen, pharmaceuticals, and substrates to organs and tissue, including the heart itself. Stroke volume (SV) of the heart depends on preload, contractility, and afterload. Preload is defined as the tension developed by the stretch of myocardial fibers. Mechanical ventilation induces changes in arterial blood pressure that, when continually or continuously measured, provide a means for assessing relative preload responsiveness. Pulmonary artery catheters are often used for measuring stroke volume (SV). However, the introduction of the pulmonary catheter itself into the blood flow can affect the value measured for stroke volume. Additionally, the use of pulmonary catheters has its own set of complications.

Arterial catheters, including arterial lines, are often used to directly measure arterial pressure, providing data for the determination of stroke volume variation (SVV), which is defined as the cyclic variation in stroke volume (SV). Stroke volume variation (SVV) is a helpful indicator in managing volume resuscitation. A patient's preload can be managed to optimize oxygen delivery, and by using cardiac output (CO) and stroke volume variation (SVV) together to manage and maintain proper perfusion of patients, including patients in surgery, the complications associated with compromised perfusion can be significantly lessened or avoided. Arterial catheters, however, are invasive, and can cause numerous complications themselves, including: ischemia, especially in the presence of arterial lesions; hemorrhage, for example in cases of catheter leakage or disconnection; and infection. In addition, depending on the particular peripheral vascular conditions in the patient, the measurements of arterial pressure may experience a poor signal-to-noise ratio, thus negatively affecting reliability.

SUMMARY OF THE INVENTION

In one embodiment of the present disclosure, a method for measuring a stroke volume variation of a subject includes providing a system for measuring cardiovascular data including an elongate member having a distal end configured for insertion within a body lumen of a subject and a proximal end configured to extend from the subject, a first expandable member carried by the elongate member, the first expandable member having a collapsed state and an expanded state and configured to be movable between the collapsed state and the expanded state by adjustment initiated externally of the subject, a first sensor disposed on a surface of the elongate member, second and third sensors disposed on a surface of the first expandable member and configured to contact a wall of the body lumen of the subject when the first expandable member is in its expanded state, and a first optical sensor located at a first location in relation to the distal end of the elongate member and configured for obtaining photoplethysmographic data, inserting the distal end of the elongate member into a lumen or duct of a patient, expanding the first expandable member such that the second and third sensors contact an internal surface of the patient, obtaining data from at least the second and third sensors to calculate two or more stroke volumes (SV) of the patient, obtaining photoplethysmographic data from the patient at least partially from the first optical sensor, and calculating a stroke volume variation (SVV) of the patient based at least in part on data obtained by the second and third sensors and the first optical sensor, wherein no data derived from intraarterial blood pressure measurement is used in the calculation.

In another embodiment of the present disclosure a method for measuring a stroke volume variation of a subject includes providing a system for measuring cardiovascular data including an elongate member having a distal end configured for insertion within a body lumen of a subject and a proximal end configured to extend from the subject, a first expandable member carried by the elongate member, the first expandable member having a collapsed state and an expanded state and configured to be movable between the collapsed state and the expanded state by adjustment initiated externally of the subject, a first electrode disposed on a surface of the elongate member, second and third electrodes disposed on a surface of the first expandable member and configured to contact a wall of the body lumen of the subject when the first expandable member is in its expanded state, and a first optical sensor located at a first location in relation to the distal end of the elongate member and configured for obtaining photoplethysmographic data, inserting the distal end of the elongate member into a lumen or duct of a patient, expanding the first expandable member such that the second and third electrodes contact an internal surface of the patient, attempting to obtain data from at least the second and third electrodes which is configured to calculate two or more stroke volumes (SV) of the patient, attempting to obtain photoplethysmographic data from the first optical sensor which is configured to calculate two or more stroke volumes, determining that one of the data from the second and third electrodes and photoplethysmographic data from the first optical sensor cannot be substantially obtained, and calculating a stroke volume variation (SVV) of the patient based on the other of the data from the second and third electrodes and photoplethysmographic data from the first optical sensor.

In another embodiment of the present disclosure a method for measuring a stroke volume variation of a subject includes providing a system for measuring cardiovascular data including an elongate member having a distal end configured for insertion within a body lumen of a subject and a proximal end configured to extend from the subject, a first expandable member carried by the elongate member, the first expandable member having a collapsed state and an expanded state and configured to be movable between the collapsed state and the expanded state by adjustment initiated externally of the subject, a first electrode disposed on a surface of the elongate member, second and third electrodes disposed on a surface of the first expandable member and configured to contact a wall of the body lumen of the subject when the first expandable member is in its expanded state, and a first optical sensor located at a first location in relation to the distal end of the elongate member and configured for obtaining photoplethysmographic data, inserting an arterial catheter having pressure measurement capabilities into an artery of the patient, inserting the distal end of the elongate member into a lumen or duct of a patient, inserting an arterial catheter having pressure measurement capabilities into an artery of the patient, expanding the first expandable member such that the second and third electrodes contact an internal surface of the patient, attempting to obtain data from the arterial catheter, attempting to obtain data from at least the second and third electrodes which is configured to calculate two or more stroke volumes (SV) of the patient, attempting to obtain photoplethysmographic data from the first optical sensor which is configured to calculate two or more stroke volumes, determining that one of the data from the arterial catheter, data from the second and third electrodes, and photoplethysmographic data from the first optical sensor cannot be substantially obtained, and calculating a stroke volume variation (SVV) of the patient based on at least one of the other two of the data from the arterial catheter, data from the second and third electrodes, and photoplethysmographic data from the first optical sensor.

In yet another embodiment of the present disclosure a system for measuring cardiovascular data includes an elongate member having a distal end configured for insertion within a body lumen of a subject and a proximal end configured to extend from the subject, a first expandable member carried by the elongate member, the first expandable member having a collapsed state and an expanded state and configured to be movable between the collapsed state and the expanded state by adjustment initiated externally of the subject, a first sensor disposed on a surface of the elongate member, second and third sensors disposed on a surface of the first expandable member and configured to contact a wall of the body lumen of the subject when the first expandable member is in its expanded state, a first optical sensor located at a first location in relation to the distal end of the elongate member and configured for obtaining photoplethysmographic data, and a processor configured to manipulate data received from at least the second and third sensors and the first optical sensor, wherein the processor is configured to calculate a stroke volume variation (SVV) of the subject based at least in part on data obtained by the second and third sensors and the first optical sensor, and without the use of any data derived from intra-arterial blood pressure measurement.

In still another embodiment of the present disclosure a system for measuring cardiovascular data includes an elongate member having a distal end configured for insertion within a body lumen of a subject and a proximal end configured to extend from the subject, a first expandable member carried by the elongate member, the first expandable member having a collapsed state and an expanded state and configured to be movable between the collapsed state and the expanded state by adjustment initiated externally of the subject, a first sensor disposed on a surface of the elongate member, second and third sensors disposed on a surface of the first expandable member and configured to contact a wall of the body lumen of the subject when the first expandable member is in its expanded state, a first optical sensor located at a first location in relation to the distal end of the elongate member and configured for obtaining photoplethysmographic data, and wherein the first expandable member in its expanded state includes a ring-shaped luminal area and is configured to interface with the subject's larynx, and the second and third sensors configured to contact tissue in proximity to the larynx when the first expandable member is in its expanded state.

In yet another embodiment of the present disclosure a system for measuring cardiovascular data includes an elongate member having a distal end configured for insertion within a body lumen of a subject and a proximal end configured to extend from the subject, the elongate member having a channel configured for the delivery of a gas, a first expandable member carried by the elongate member, the first expandable member having a collapsed state and an expanded state and configured to be movable between the collapsed state and the expanded state by adjustment initiated externally of the subject, a first sensor disposed on a surface of the elongate member, second and third sensors disposed on a surface of the first expandable member and configured to contact a wall of the body lumen of the subject when the first expandable member is in its expanded state, a first optical sensor located at a first location in relation to the distal end of the elongate member and configured for obtaining photoplethysmographic data, and wherein the first expandable member in its expanded state is configured to interface with the subject's larynx for delivery of at least oxygen gas through the lumen of the elongate member and into the respiratory system of the subject, and the second and third sensors configured to contact tissue in proximity to the larynx when the first expandable member is in its expanded state.

In still another embodiment of the present disclosure a system for measuring cardiovascular data includes an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the throat of the subject, second and third sensors disposed on a surface of the first expandable member and configured to contact tissue in proximity to the larynx when the first expandable member is in its expanded state, and a first optical sensor carried on the elongate member and configured for obtaining photoplethysmographic data.

In yet another embodiment of the present disclosure a system for measuring cardiovascular data includes an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the throat of the subject, second and third sensors disposed on a surface of the first expandable member and configured to contact tissue in proximity to the larynx when the first expandable member is in its expanded state, a first optical sensor carried on the elongate member and configured for obtaining photoplethysmographic data, and a second optical sensor located at a second location, different from the first location.

In still another embodiment of the present disclosure a system for measuring cardiovascular data includes an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the throat of the subject, second and third sensors disposed on a surface of the first expandable member and configured to contact tissue in proximity to the larynx when the first expandable member is in its expanded state, and a first optical sensor located at a first location in relation to the first expandable member and configured for obtaining photoplethysmographic data, wherein the first optical sensor is remotely located from the elongate member.

In yet another embodiment of the present disclosure a method for measuring at least one of cardiac output and stroke volume variation of a subject includes providing a system for measuring cardiovascular data including an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the throat of the subject, second and third sensors disposed on a surface of the first expandable member and configured to contact tissue in proximity to the larynx when the first expandable member is in its expanded state, and a first optical sensor carried on the elongate member and configured for obtaining photoplethysmographic data, wherein the first optical sensor is remotely located from the elongate member, inserting the distal end of the elongate member into the throat of a patient, expanding the first expandable member such that at least one of the second and third sensors contact a portion of the subject in proximity to the larynx of the patient, obtaining photoplethysmographic data from the patient at least partially from the first optical sensor, and calculating at least one of cardiac output and stroke volume variation of the patient.

In still another embodiment of the present disclosure a system for measuring cardiovascular data includes an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the body lumen of the subject, second and third sensors disposed on a surface of the first expandable member and configured to contact a wall of the body lumen when the first expandable member is in its expanded state, and a first optical sensor carried on the elongate member and configured for obtaining photoplethysmographic data.

In yet another embodiment of the present disclosure a system for measuring cardiovascular data includes an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the body lumen of the subject, second and third sensors disposed on a surface of the first expandable member and configured to contact a wall of the body lumen when the first expandable member is in its expanded state, a first optical sensor located at a first location in relation to the first expandable member and configured for obtaining photoplethysmographic data, and a second optical sensor located at a second location, different from the first location.

In still another embodiment of the present disclosure a system for measuring cardiovascular data includes an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the body lumen of the subject, second and third sensors disposed on a surface of the first expandable member and configured to contact a wall of the body lumen when the first expandable member is in its expanded state, and a first optical sensor located at a first location in relation to the first expandable member and configured for obtaining photoplethysmographic data, wherein the first optical sensor is remotely located from the elongate member.

In yet another embodiment of the present disclosure a method for measuring at least one of cardiac output and stroke volume variation of a subject includes providing a system for measuring cardiovascular data including an elongate member having a distal end configured for insertion within a body lumen of a subject and a proximal end configured to extend from the subject, a first expandable member coupled at or near the distal end of the elongate member, the first expandable member having a collapsed state and an expanded state and movable between the collapsed state and the expanded state by adjustment performed adjacent the proximal end of the elongate member, a first sensor disposed on a surface of the elongate member and configured to be placed inside the body lumen of the subject, second and third sensors disposed on a surface of the first expandable member and configured to contact a wall of the body lumen when the first expandable member is in its expanded state, and a first optical sensor located at a first location in relation to the first expandable member and configured for obtaining photoplethysmographic data, wherein the first optical sensor is remotely located from the elongate member, inserting the distal end of the elongate member into a lumen or duct of a patient, expanding the first expandable member such that at least one of the second and third sensors contact a portion of the subject, obtaining photoplethysmographic data from the subject at least partially from the first optical sensor, and calculating at least one of cardiac output and stroke volume variation of the subject.

DETAILED DESCRIPTION OF THE ILLUSTRATED EMBODIMENTS

Figure 1:
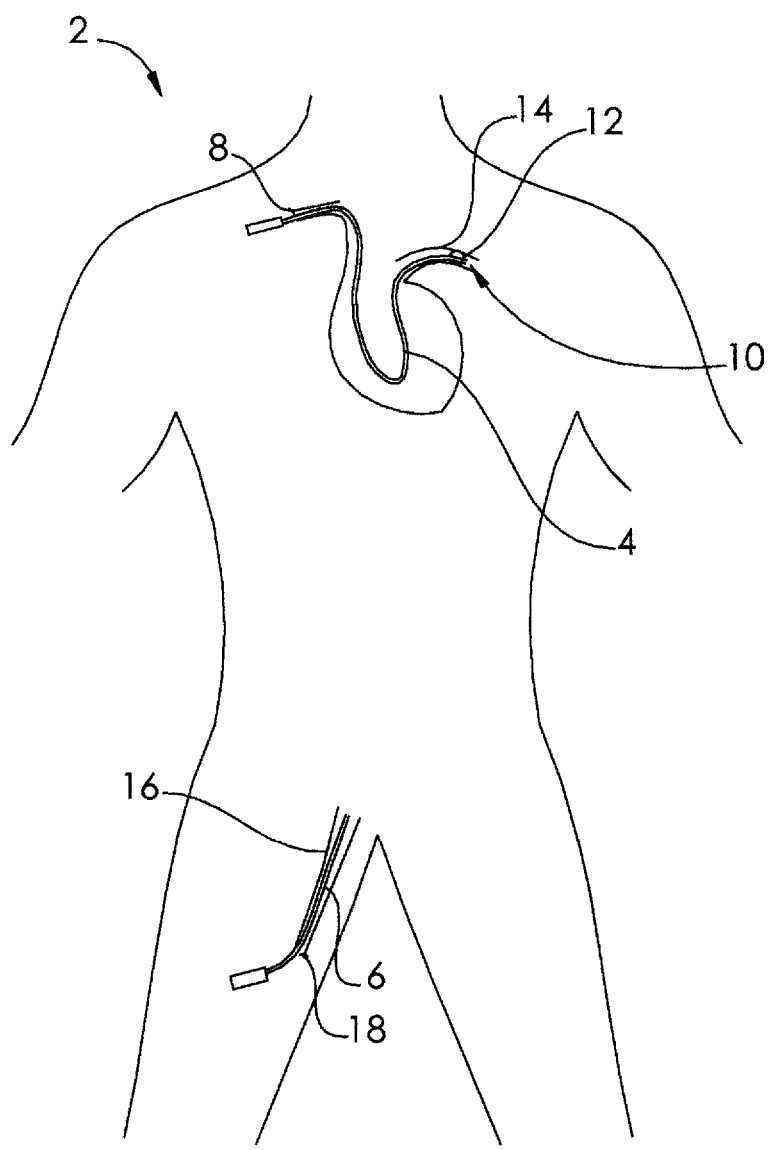
FIG. 1 is a plan view of a patient undergoing cardiovascular monitoring.

Embodiments of the invention include an approach for acquiring signals for measuring important parameters of the heart, including signals obtained via measurement from at least one or more portions of the body of a subject that do not include the skin. The one or more portions of the body can include internal portions of the body, such as portions within naturally occurring orifices or body cavities or lumens, or even a cavity of the body caused by trauma. In certain embodiments, one or more electrically conductive "sensor" pads or electrodes are deposited on, printed to, or attached to a sensing device that is configured to be inserted into a body orifice, cavity or lumen. Some examples of body lumens include, but are not limited to the trachea, bronchi, esophagus, or throat of a patient, including tissue in the vicinity of the larynx. In addition to the sensors on the sensing device, one or more auxiliary sensor may also be used. The one or more auxiliary sensor may be placed in contact with one or more other portions of the body which allow contact with the subject's mucosa (i.e., mucous membrane). The sensors may be carried on the sensing device on a surface comprising a membrane, balloon, or cuff that can be inflated to press the sensors into contact with the mucosal lining of the trachea, bronchi, esophagus, throat, including tissue in the vicinity of the larynx. The sensors may also be carried on an elongate member of the sensing device (body, shaft), which may be configured to be changed from a linear or substantially linear low-profile state to an expanded state having an enlarged state in comparison with the elongate member of the sensing device. The use of a sensing device which comprises sensors for placement on internal structures has the benefit of placing the sensors in contact with electrically conductive moist tissue, thus allowing immediate, reliable electrical coupling. Such a device can be quickly placed into a body lumen, cavity or orifice, and expanded (e.g., inflated) thereby immediately acquiring the desired signals. The sensors may be electrodes configured to measure bio-impedance of tissue.

One or more additional sensors comprising optical sensors are carried on the sensing device, and are configured to transmit multiple wavelengths of optical radiation into a tissue site of the subject and detect the optical radiation after attenuation by pulsatile blood flow flowing within the tissue site so as to generate a sensor signal responsive to the detected optical radiation. Signals are obtained both from the bio-impedance sensors (electrodes) and the optical sensors may provide data that is used to determine values for important cardiovascular parameters.

A system for measurement of cardiovascular data includes a sensing device that takes the place and performs the functions of standard airway devices used in mechanical ventilation. As many patients requiring the measurement of cardiovascular parameters typically receive either a tracheal tube (endo-tracheal tube), a nasogastric tube (NG tube), or a laryngeal tube, there is no increased invasiveness of this procedure. Besides the endo-tracheal tube, NG tube, or laryngeal mask, other types of devices may be incorporated into the sensing devices taught herein, such as a gastric lavage tube, a gastric aspiration tube, or a gastric decompression tube, including, but not limited to an Ewald orogastric tube, a Lavacutor® orogastric tube, an Edlich orogastric tube, a sump tube, such as a Salem tube, a Levin tube, gastric suction/feeding tubes, such as a Moss Mark IV nasal tube, a Dobbhoff nasojejunal feeding and gastric decompression tube, a nasointestinal tube such as a Miller-Abbott tube, and a treatment tube such as a Sengstaken-Blakemore tube.

FIG. 1 illustrates a patient 2 with a pulmonary artery catheter 4 and an arterial catheter 6 in place and being utilized for cardiovascular monitoring. The pulmonary artery catheter 4 is inserted through an insertion site 8 and has a distal end 10 having a balloon 12 which is configured to be advanced to a pulmonary artery 14. The balloon 12 is inflated, for example, within a small pulmonary artery branch, to measure a pulmonary artery wedge pressure. The pulmonary artery wedge pressure may be used as an indirect estimate of left atrial pressure. Possible complications from pulmonary artery catheters include pneumothorax, hematoma, arrhythmia, pulmonary thrombosis, infarction, endothelial damage, valve damage, bacteremia, vessel rupture, infection, and hemorrhage. The pressures measured by the pulmonary artery catheter 4 can be reliable, but may also be subject to dampening from the system of the catheter lumen, connectors, and other elements in the path.

The arterial catheter 6 comprises a tube having a lumen, and may be placed via an insertion site 18 into any number of arteries in the body, for example, an artery 16 in the peripheral circulation. Arteries may include: radial, ulnar, brachial, axillary, posterior tibial, femoral, and dorsalis pedis arteries. The lumen of the arterial catheter may be used to measure arterial pressure, and may also be used to obtain samples of arterial blood. As described, arterial catheters 6 can cause complications such as ischemia, especially in the presence of arterial lesions; hemorrhage, for example in cases of catheter leakage or disconnection; and infection. In addition, depending on the particular peripheral vascular conditions in the patient, the measurements may experience a poor signal-to-noise ratio, thus negatively affecting reliability. The measurements may also be subject to dampening from the system of the catheter lumen, connectors, and other elements in the path.

Figure 2:
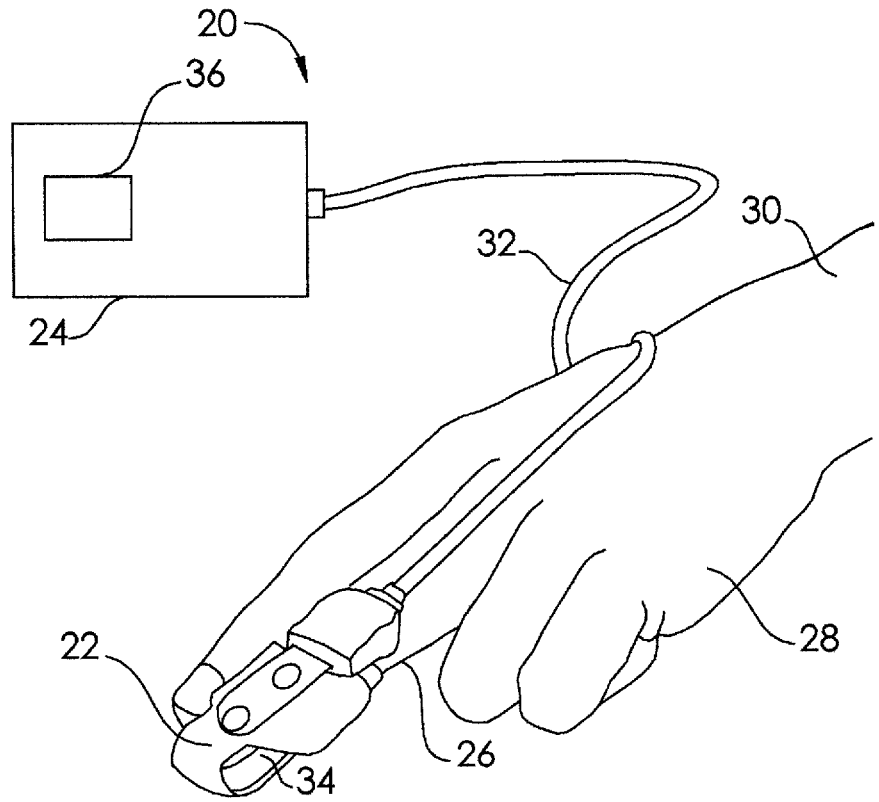
FIG. 2 is a perspective view of a system for cardiovascular monitoring on the hand of a patient.

FIG. 2 illustrates a system for physiological monitoring 20 including an optical sensor 22 and a monitor 24. The optical sensor 22 is configured to be coupled to the finger 26 of a hand 28 of a subject 30, and is connected to the monitor 24 by a cable 32. The optical sensor 22 is a pulse oximeter having light emitting diodes (LEDs) and a detector. The LEDs transmit optical radiation into a tissue site 34, and the detector responds to the intensity of the optical radiation after absorption by pulsatile blood flow within the tissue site 34. The optical sensor may use pulse oximetry for measuring physiological parameters such as pulse rate (PR) and oxygen saturation ($SpO_2$). The monitor 24 is configured to display the physiological parameters on a display 36, and may also display a plethysmograph, which tracks continuous blood pressure.

Figure 3:
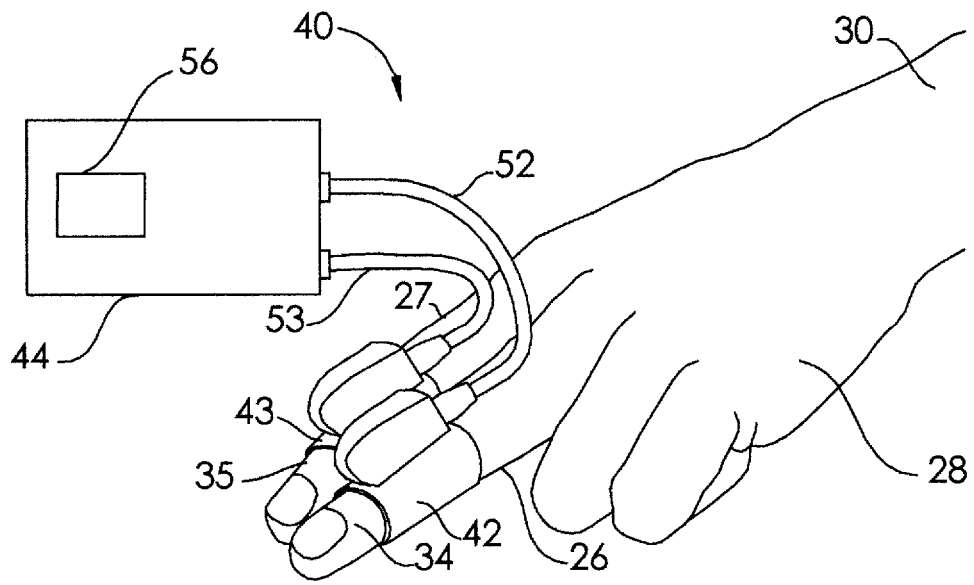
FIG. 3 is a perspective view of a system for cardiovascular monitoring on the hand of a patient.

FIG. 3 illustrates a system for physiological monitoring 40 including a first finger cuff 42, a second finger cuff 43, and a monitor 44. The finger cuffs 42, 43 are coupled to be coupled to fingers 26, 27 of a hand 28 of a subject 30, and are each connected, respectively, to the monitor 44 by cables 52, 53. The finger cuffs 42, 43 are configured to be inflatable to track continuous blood pressure at one or more tissue sites 34, 35. The monitor is configured to display data obtained from the finger cuffs 42, 43 on a display 56.

Several methodologies are currently utilized to determine, calculate, or estimate cardiac output (CO) and stroke volume variation (SVV), though they are not optimal. The methodologies for obtaining CO and SVV values include: A) pulse contour analysis of a peripheral blood pressure waveform (e.g., taken from an invasive arterial catheter/line 6), B) contour analysis of a blood pressure wave form from peripheral vessels (e.g., taken from a finger-mounted optical sensor 22, such as a finger sensor used in pulsed oximetery), C) contour analysis of a blood pressure wave form from peripheral vessels using finger cuffs 42, 43, and D) external bio-impedance, such as thoracic bio-impedance, which utilizes several electrodes placed on the skin of the lower thorax and the neck to measure the amount of thoracic fluid. All of these methods are susceptible to peripheral vascular conditions in both healthy and diseased states, and may be subjected to problems of a poor signal-to-noise ratio. Other methods being used for cardiac output (CO) include internal bio-impedance, and transesopageal Doppler (TEE). Doppler systems are often expensive, and require additional information that is often not available, for example the exact diameter and morphology of the blood vessels.

Figure 4:
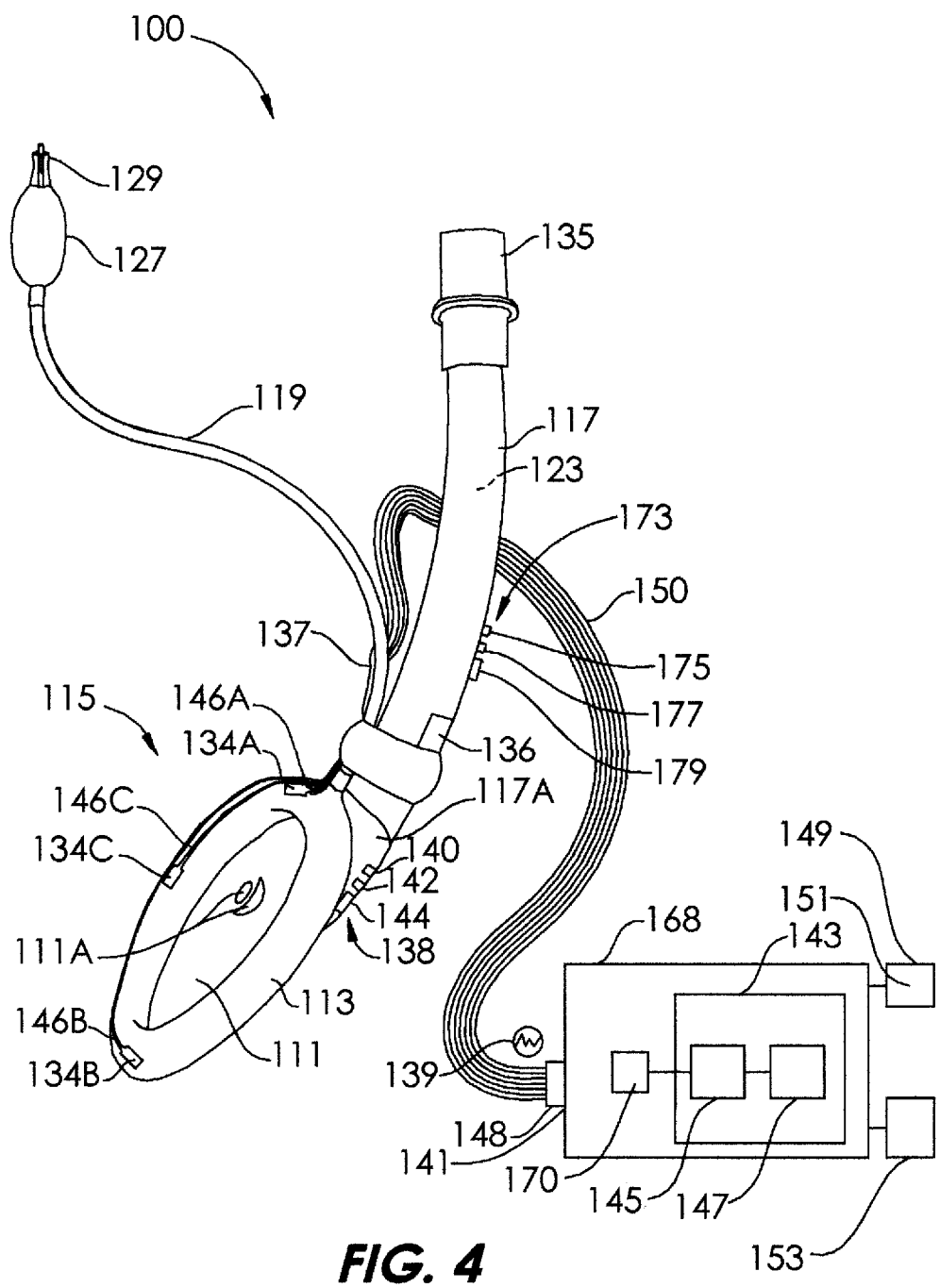
FIG. 4 is a system for cardiovascular sensing including a laryngeal mask, according to an embodiment of the present disclosure.

A system for measurement of cardiovascular parameters 100 is illustrated in FIG. 4. The system for measurement of cardiovascular parameters 100 includes a sensing device which is a laryngeal mask or laryngeal airway (LMA) 115 having sensing capabilities. One method to maintain an oral airway during anesthetic management or mechanical ventilation, utilizes a laryngoscope for endotracheal intubation. Alternatively, a laryngeal mask airway can be inserted into the larynx. A laryngeal mask or laryngeal mask airway (LMA) 115, as shown in FIG. 4, and comprises an oval mask body 111 and a hollow cuff 113 which engages the periphery of the mask body 111 and has a ring-shaped luminal area. The hollow cuff 113 may follow the oval shape of the mask body 111. A respiratory tube 117 is connected to a tube connecting portion 117A on the outside surface of the mask body 111. The respiration is performed through the holes 111A which are formed in the mask body 111, and through an elongate passageway 123 in the respiratory tube 117. A fitting 135 is sealingly attached to the respiratory tube 117 and is configured for coupling to mechanical ventilation equipment. The fitting 135 is configured to couple to a respiratory or other oxygen or air delivery apparatus, for delivering oxygen and other gases, which may in some cases include an anesthetic, through the respiratory passageway 123 and out the holes 111A and then into the patient's lungs. An inflation tube 119, fluidly coupled to the cuff 113, is configured for injecting air into the cuff 113. A valve 127 carried in fluid communication with the inflation tube 119 may be used to maintain the pressurized air within the cuff 113. In some embodiments, the valve 127 may be a one-way valve (open or closed). In some embodiments, the valve 127 may be a pinch valve, which is normally in a closed condition be may be pinched to allow air to enter or exit the inflation tube 119. In some embodiments, the valve 127 may be a luer-activated valve which allows air to enter of exit the inflation tube 119 when a luer or a syringe (not shown) is attached to a luer connector 129 at the end of the inflation tube 119. Prior to insertion of the LMA 115, an anesthesiologist or other medical professional deflates the cuff 113 by extracting air therefrom. Once the anesthesiologist or other medical professional inserts the LMA 115 into a patient's larynx, he or she then inflates the cuff 113 by introducing air therein. In this manner, an airway is maintained by covering the larynx with the LMA 115.

Figure 5:
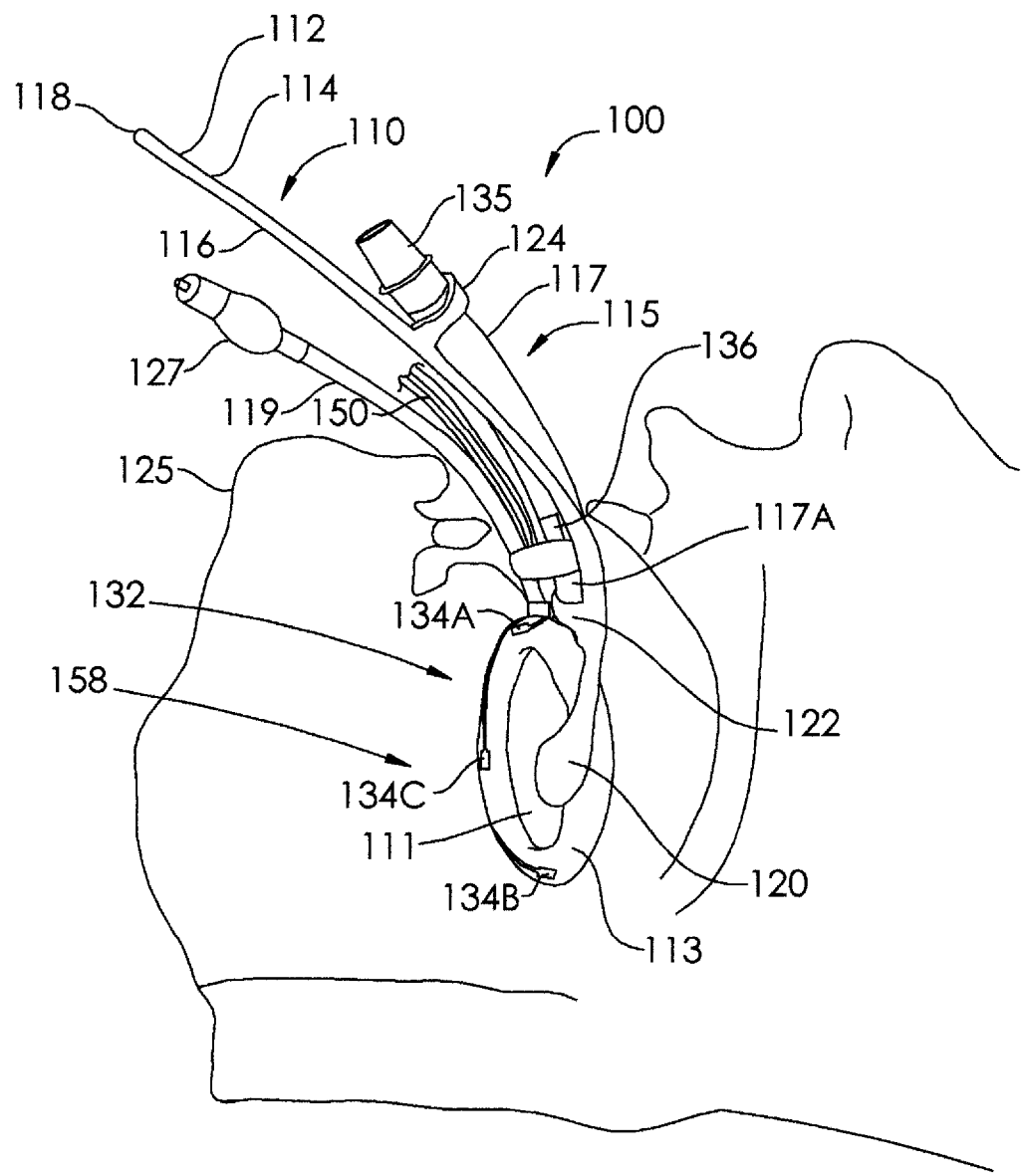
FIG. 5 is a partial sectional view of the laryngeal mask of FIG. 4 being inserted into a subject.

The LMA 115 is shown in FIG. 5 being inserted into the larynx 158 of a patient 125 using an insertion guide 110. The insertion guide 110 may comprise an elongated curved member 112, having a substantially circular or non-circular cross section. The member 112 may be fabricated from a rigid material having flexible qualities, such as a plastic or a composite having shape-memory. In some embodiments, the member 112 has opposing distal and proximate surfaces 114, 116, the surfaces being defined respective to an anesthesiologist inserting the LMA 115. A rounded top end portion 118 of the member 112 may serve as a handle for an anesthesiologist to use in manipulating the insertion guide 110. A bottom end portion 120 may have a general scoop shape. The bottom end portion 120 may be rounded, flat and curved, so as to fit the distal surface of LMA mask body 111, as shown in FIG. 4.

A curved fulcrum member 122 may extend from the proximate surface 116 of the member 112, near the bottom end portion 120. The fulcrum member 122 may be dimensioned to snugly fit over the tube-connecting portion 117A of the LMA 115. Between the bottom end portion 120 and the fulcrum 122, the member 112 may curve to conform to the distal portion 132 of the LMA 115, as shown in FIG. 5. A curved holder member 124 may extend from the distal surface 114 of the member 112, and may be located closer to top end portion 118 than the fulcrum 122. The holder 124 is dimensioned to fit over the portion of the respiratory tube 117 farthest from LMA mask body 111, also shown in FIG. 5.

In use, an anesthesiologist or other medical professional may fit the insertion guide 110 onto the LMA 115 by securing the fulcrum 122 in place on the tube-connecting portion 117A of the LMA 115 and by also securing the holder 124 in place on the portion of the LMA respiratory tube 117 farthest from LMA mask body 111, so that the bottom end portion 120 engages the distal portion of the LMA mask body 111. The anesthesiologist then inserts the LMA 115 with the guide 110, into the larynx 158 of the patient 125, using the rounded top end portion 118 as a handle, as shown in FIG. 5.

Once the LMA 115 has been inserted, the anesthesiologist may use the guide 110 to properly place the LMA 115, specifically the LMA mask body 111, within the larynx 158 of the patient 125. In doing so, the anesthesiologist may use the holder 124 and the bottom end portion 120 to bend the LMA 115, shown bent in FIG. 4, and simultaneously may use the fulcrum 122 to push the LMA 115 down into the patient's throat, to insure proper placement therein. The angle and shape of bottom end portion 120 also allows an anesthesiologist to better manipulate the tip of the LMA 115 at the larynx 158 and position it properly there.

Figure 6:
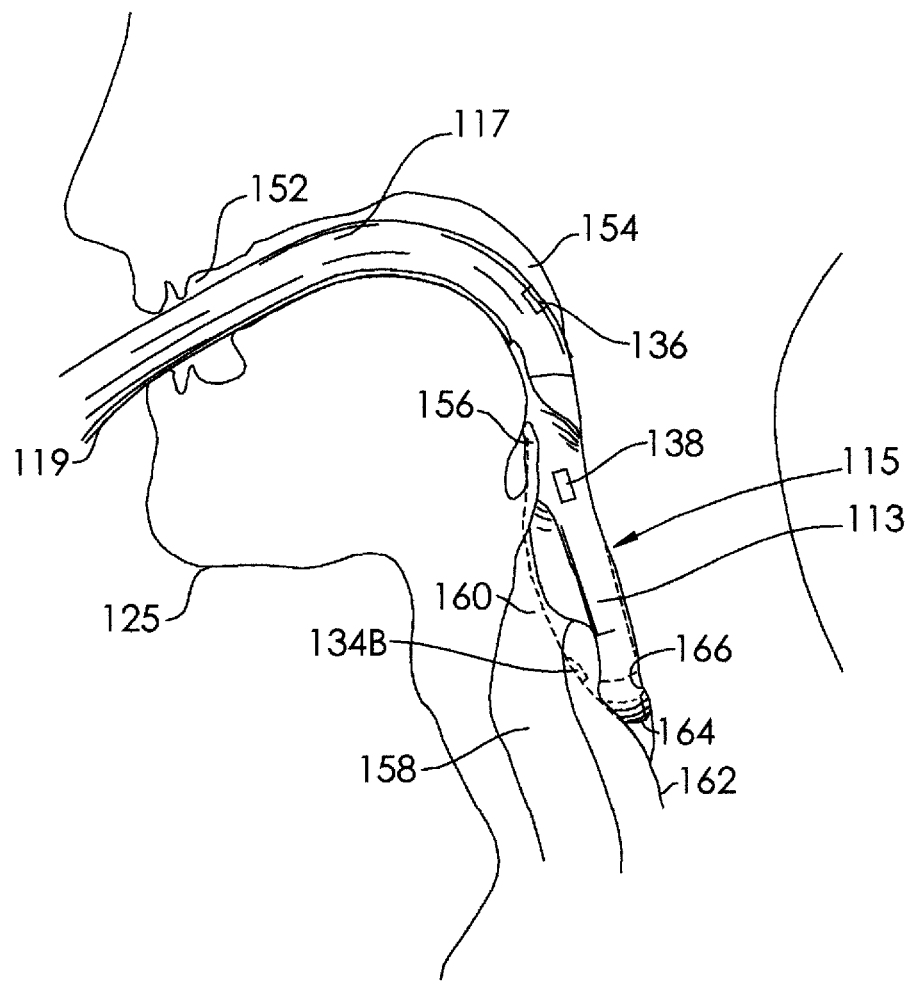
FIG. 6 is a partial sectional view of the laryngeal mask of FIG. 4 in place within a subject.

After the anesthesiologist positions the LMA 115 so that it covers the larynx 158 of the patient 125, the anesthesiologist can disengage the holder 124 and the fulcrum 122 from their respective points on the LMA 115 by angularly rotating the device, whereupon the anesthesiologist can easily remove LMA guide 110 from the throat 154 (FIG. 6) of the patient 125, leaving the LMA 115 in place. The slender, curvilinear structure of member 112 allows the anesthesiologist to remove LMA guide 110 without widening the device or otherwise complicating its backward passage through the throat and mouth of the patient 125, thereby making it safer for insertion therein, and more efficient for anesthesiologist use. A number of alternative insertion and placement methods may be used in place of the one described herein. The LMA 115 is shown in FIG. 6 inserted through the mouth 152 of the patient 125 and in place within the throat 154 of the patient 125. The distal end 164 of the LMA 115 is shown adjacent the base 166 of the throat 154, with the cuff 113 shown in relation to the epiglottis 156 and the larynx 158, including the inlet 160 of the larynx. The esophagus 162 is also shown for reference purposes.

The LMA 115 incorporates one or more sensors, which may include one or more cuff-based sensors 134 (134A, 134B, 134C), and one or more tube-based sensors 136. The number of sensors 134, 136 on the cuff 113 and/or the tube 117 (which may include the tube connecting portion 117A) may be varied in different embodiments. In addition, an optical sensor 138 (for example, a pulsed oximetry device) having at least two light emitting sources 140, 142 and one light detector 144, is mounted on the mask body 111 and/or the tube 117/tube connecting portion 117A (shown on the tube connecting portion 117A in FIG. 4). The optical sensor 138 may even be located on the cuff 113, for example, a rearwardly-facing portion of the cuff 113 that does not directly engage tissue of the body lumen when the cuff 113 is inflated. The optical sensor 138 is configured to obtain plethysmographic data when it is positioned in spaced relation with tissue, for example, in a non-contact arrangement with an inner wall of a body lumen. The sensors 134, 136 may comprise electrodes and utilize bio-impedance to generate waveforms representative of the flow of blood through the carotid arteries. Examples of bioelectrical impedance analysis of blood flow using electrode sensors arrayed within body lumens, at least some of the sensors contacting mucosal tissue can be found in U.S. Pat. No. 5,791,349, issued on Aug. 11, 1998, and entitled "APPARATUS AND METHOD OF BIOELECTRICAL IMPEDANCE ANALYSIS OF BLOOD FLOW," U.S. Pat. No. 5,782,774, issued on Jul. 21, 1998, and entitled "APPARATUS AND METHOD OF BIOELECTRICAL IMPEDANCE ANALYSIS OF BLOOD FLOW," U.S. Pat. No. 6,095,987, issued on Aug. 1, 2000, and entitled "APPARATUS AND METHODS OF BIOELECTRICAL IMPEDANCE ANALYSIS OF BLOOD FLOW," U.S. Pat. No. 6,292,689, issued on Sep. 18, 2001, and entitled "APPARATUS AND METHODS OF BIOELECTRICAL IMPEDANCE ANALYSIS OF BLOOD FLOW," all of which are hereby incorporated by reference in their entirety for all purposes.

The location of the LMA 115 when it is engaged with (around) the larynx 158 allows the sensors 134 and optical sensor 138 to be in proximity to the carotid arteries, particularly, the common carotid arteries, which deliver a sizeable volume of blood in a pulsatile manner. The sensors 134 are configured to contact tissue in the vicinity of the larynx 158 when the cuff 113 is inflated and the LMA 115 is engaged with the larynx 158. The sensors 134, 136 are also used to obtain an electrocardiogram signal from the body of the patient to provide electrical timing information, as described in U.S. provisional application No. 62/159,912, filed May 11, 2015, and entitled "SYSTEMS AND METHODS FOR INTERNAL ECG ACQUISITION," and international publication number WO2016/179563, published on Nov. 10, 2016, and entitled "SYSTEMS AND METHODS FOR INTERNAL ECG ACQUISITION," both of which are hereby incorporated by reference in their entirety for all purposes. By acquiring one or more electrocardiogram signals from an internal portion of a subject, externally-placed (e.g., skin) electrodes may often be avoided. A number of subjects may have burns or trauma on portions of their body, including the torso and limbs, which makes placement of external ECG electrodes challenging and sometimes impossible. The sensors 134, 136 and/or additional conductive traces 146A, 146B, 146C may be painted, sprayed, or printed on the cuff 113, the tube 117, or even the inflation tube 119, for example, by the methods described in U.S. provisional application No. 62/158,504, filed May 7, 2015, and entitled "FLEXIBLE ELECTRIC CIRCUIT ON FLEXIBLE MEMBRANES," international publication number WO2016/179563, published on Nov. 10, 2016, and entitled "SYSTEMS AND METHODS FOR INTERNAL ECG ACQUISITION," and U.S. Pat. No. 9,289,141, issued on Mar. 22, 2016, and entitled "APPARATUS AND METHODS FOR THE MEASUREMENT OF CARDIAC OUTPUT," all of which are hereby incorporated by reference in their entirety for all purposes. The conductive traces 146A, 146B, 146C connect the sensors 134, 136 (e.g., electrodes) to a multi-contact connector 148 via an extension 150 which may contain conductive wires or traces. In some embodiments, a flex circuit 137 may be used to couple the conductive traces 146A, 146B, 146C (by solder, for example) to the extension 150.

The system for measurement of cardiovascular parameters 100 described herein is useful to measure physiological functions/parameters in mammalian subjects, including stroke volume, cardiac output, and stroke volume variation. Once the cuff 113 is positioned and expanded, a current is injected into the subject's tissue through one of the electrodes (sensors 134, 136) serving as a current electrode. A voltage is established between the current electrode and the ground electrode (one of sensors 134, 136) so that a current flows through the tissue disposed between the current electrode and the ground electrode. With one or more sense electrodes (sensors 304), the voltages caused by the current flowing in the tissue are detected, wherein the voltages vary in accordance with changes in the bioelectrical impedance of the tissue.

The stroke volume variation (SVV) for a single respiratory cycle may be determined by the following equation:

$$SVV = \frac{(SV_{MAX}) - (SV_{MIN})}{(SV_{MEAN})}$$

In some embodiments, the $SV_{MEAN}$ is determined by the following equation:

$$SV_{MEAN} = \frac{1}{2} \times (SV_{MAX} + SV_{MIN})$$

In other embodiments, the $SV_{MEAN}$ may be determined by taking the average (mean) of all of the stroke volumes within the single respiratory cycle. In other embodiments, the $SV_{MEAN}$ may be determined by removing some of the stroke volumes within a single respiratory cycle (e.g., one or more outliers) and then taking the average (mean) of all of the remaining stroke volumes.

In still other embodiments, the stroke volume variation (SVV) for a single respiratory cycle may be determined by the following equation:

$$SVV = \frac{(SV_{MAX}) - (SV_{MIN})}{(SV_{MIN})}$$

Stroke volume variation may be given or displayed as a percentage.

Heart rate (HR) may be obtained from electrocardiogram data from the bio-impedance sensing (e.g., R-Wave to R-Wave interval) or from dicrotic notch to dicrotic notch interval measurement in bio-impedance data or pulse (optical sensor) data.

The connector 148 may be configured to be coupled to an input 141 of a console 168 and is configured to carry signals 139 from the one or more sensors 134, 136 and first optical sensor 138 to the console 168. In some embodiments, the console 168 may include an analog-to-digital converter 170 through which the one or more signals 139 are converted. In some embodiments, the signals 139 may be multiplexed. The one or more signals 139 may enter a processor 143 provided by the console 168. The processor 143 may include one or more amplifiers 145 for amplifying the signal 139 and one or more filters 147 for filtering the signal 139. A display 149 is configured to display a resulting graphic representation 151. The graphic representation 151 may simply be a parameter value or a table of values, or may actually be a graph of data, for example a plethysmograph. The display 149 may be built in to the console 168 or may be separate. The display 149 may be directly connected to the console 168 or may be remote and communicate wirelessly. The console 168 may include an interface 153 which allows a user to control and/or communicate with the console 168 or the system for measurement of cardiovascular parameters 100 in general. The interface 153 may even allow a user to control or communicate with the LMA 115, for example, if the LMA 115 incorporates an internal microprocessor, which may be carried on a flex circuit. The interface 153 may be a touch screen, a keyboard, an audio communication system (e.g., voice-activated), and may incorporate a graphic user interface (GUI). The processor 143 is configured to calculate one or more value, including but not limited to, stroke volume, heart rate, and $SpO_2$ from photoplethysmographic data provided by the first optical sensor 138 and the electrocardiogram signal and blood flow information provided by the first, second, and third sensors 134A, 134B, 134C. The emitters 140, 142 and detector 144 of the first optical sensor 138 function as a pulse oximetry device to obtain a photoplethysmograph from the throat or oral cavity by the transmission of optical radiation into a tissue site (tissue at the wall of the throat 154, adjacent or at the same level as the carotid arteries), and the detection of the intensity of the optical radiation after absorption by pulsatile blood flow within the tissue site. All three signals (waveforms representative of blood flow, electrocardiogram signal, photoplethysmograph) are utilized to calculate the stroke volume, heart rate, and $SpO_2$ (peripheral capillary oxygen saturation) and to obtain waveforms representative of the arterial flow of central vessels which in this example are one or more of the carotid arteries, but may alternatively be other blood vessels. As previously described, cardiac output (CO) is calculated by multiplying stroke volume (SV) by heart rate (HR). When coupled with the values provided by an external blood pressure cuff, real time estimates of arterial blood pressure can also be obtained.

This approach eliminates the need for a peripheral blood pressure waveform. No invasive arterial line is needed, thus avoiding potential complications of arterial lines, including: permanent ischemic damage, temporary occlusion, sepsis, local infection, pseudoaneurysm, hematoma, bleeding, or other effects. By using only waveforms generated from body core vessels all of the limitations of peripheral monitoring (due, for example, to peripheral artery disease, vaso-spasm, changes in vascular tone, poor peripheral circulation, poor body temperature, etc.) can be avoided.

In some alternative embodiments, the emitting sources 140, 142 of the optical sensor 138 may be configured to emit through the cuff 113 and the detector 144 may be configured to receive back reflectance information. In some embodiments, the two light emitting sources 140, 142 and one light detector 144 of the optical sensor 138 (or emitting sources or detector in additional optical sensors) may be located on the tube 117 or inflation tube 119 and work by using reflectance methodology from an internal body lumen surface. In some alternative embodiments, a second optical sensor 173 having two light emitting sources 175, 177 and one light detector 179 may be located on a distal portion, or on a more centrally-located portion (as shown in FIG. 4) of the LMA 115, and may be used in conjunction with sensors that are internally located, to allow for the calculation of cardiac output, stroke volume variation and/or other cardiac metrics.

Figure 7:
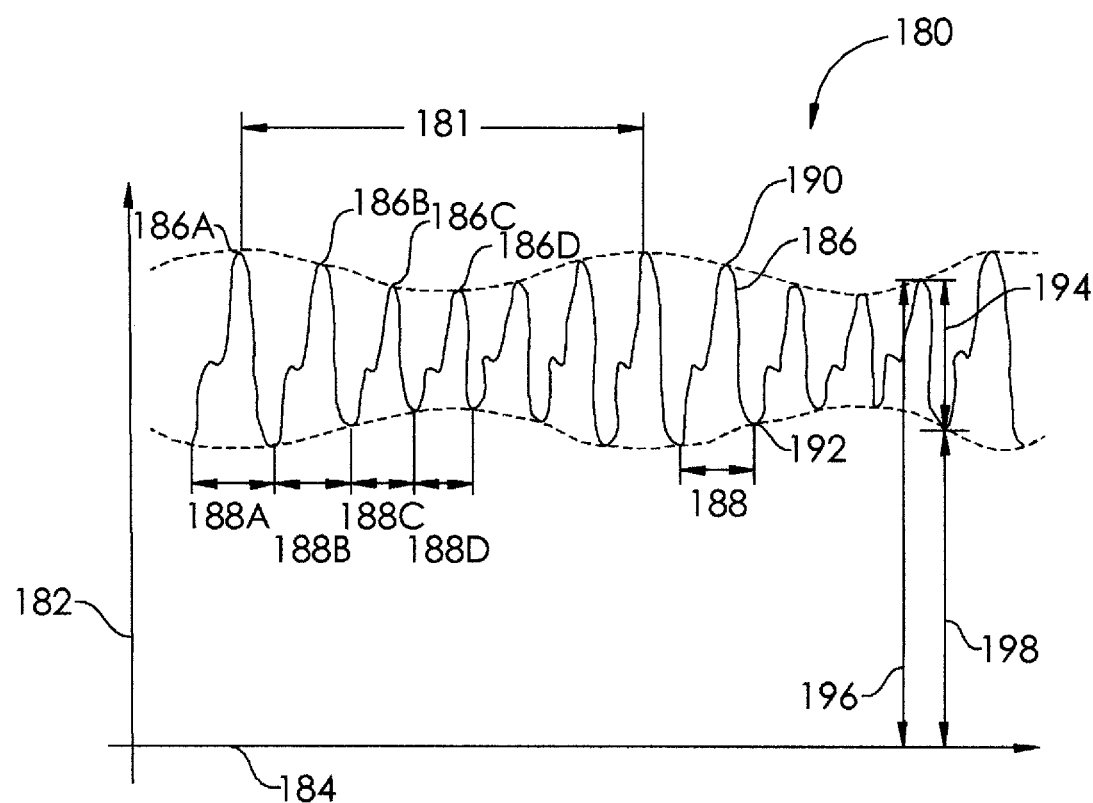
FIG. 7 is a plethysmograph indicating respiratory-induced variation.

FIG. 7 illustrates a plethysmograph 180, obtained from data acquired by the optical sensor 138 and which may be displayed on the display 149 of the console 168. The plethysmograph 180 graphs amplitude over time, and is plotted in relation to an amplitude axis 182 and a time axis 184. The amplitude varies depending on the pulsatile nature of blood within tissue in the target site. In the particular case of the system for measurement of cardiovascular parameters 100 illustrated in FIG. 4, this target site is an area adjacent the carotid arteries whose pulsatile flow causes a cyclic variance in light absorption. The plethysmograph 180 includes a plurality of pulses 186A, 186B, 186C, 186D, each having a pulse time period 188A, 188B, 188C, 188D. Each pulse includes a peak 190 and a valley 192. A pulse height 194 for a particular pulse is equal to the difference between a pulse peak amplitude 196 and a pulse valley amplitude 198 for that pulse. The largest pulse 186A and the smallest pulse 186D of a particular respiratory cycle 181 can be used in the calculation of stroke volume variation (SVV). The respiratory cycle 181 includes an inspiration peak and an expiration peak, with the largest pulse 186A and smallest pulse 186D commonly occurring from these two peaks. A series of stroke volumes (SV) are obtained from data from at least two of the sensors 134A, 134B, 134C. The number of stroke volume (SV) measurements taken in a single respiratory cycle may typically be between two and twelve, or in some embodiments between three and ten. The maximum numbers of stroke volume (SV) measurements possible within a single respiratory cycle may be less than ten, depending also upon the heart rate (HR) and the respiration rate.

The stroke volume variation (SVV) for a single respiratory cycle may be determined by the following equation:

$$SVV = \frac{\text{(Pulse height of largest pulse)} - \text{(Pulse height of smallest pulse)}}{\text{(Mean pulse height)}}$$

In some embodiments, the Mean pulse height (MPH) is determined by the following equation:

MPH=½×(Pulse height of largest pulse+Pulse height of smallest pulse)

In other embodiments, the Mean pulse height (MPH) may be determined by taking the average (mean) of all of the two or more pulse heights within the single respiratory cycle. In other embodiments, the Mean pulse height (MPH) may be determined by removing some of the pulses (or pulse height measurements) within a single respiratory cycle (e.g., one or more outliers) and then taking the average (mean) of all of the remaining pulse heights.

In still other embodiments, the stroke volume variation (SVV) for a single respiratory cycle may be determined by the following equation:

$$SVV = \frac{\text{(Pulse height of largest pulse)} - \text{(Pulse height of smallest pulse)}}{\text{(Pulse height of smallest pulse)}}$$

Besides calculating a stroke volume variation (SVV) value from either data obtained either via bio-impedance or via plethysmography (from sensors 134, 136 or optical sensor 138, respectively) additional parameters may be derived, such as systolic pressure variation (SPV), and its related components: deltaUp and deltaDown.

As described, the system for measurement of cardiovascular parameters 100 thus has two parallel mechanisms to determine stroke volume variation (SVV). The processor 143 may calculate a stroke volume variation (SVV) value using data obtained via bio-impedance from the sensors 134, 136 and may calculate a stroke volume variation (SVV) value using data obtained via plethysmography from the optical sensor 138. Neither of these two methodologies of obtaining stroke volume variation (SVV) require invasive arterial catheters. In addition, having both avenues of obtaining data to make a stroke volume variation (SVV) calculation is extremely helpful in many clinical situations, wherein either of the two modalities (bio-impedance measurement or plethysmography) may temporarily be interrupted or corrupted. In these cases, the other, uninterrupted modality would remain available and would thus continue to allow a stroke volume variation (SVV) measurement (and any other related measurement within its capability). For example, many additional procedures may be performed on subjects on which the system for measurement of cardiovascular parameters 100 is being used. Electrocautery may at times interrupt or interfere with signals received during bio-impedance measurement. If a stroke volume variation (SVV) value is being calculated based on bio-impedance data, an interruption of the bio-impedance data collection or data quality may signal the processor 143 to start using the plethysmography data to calculate the stroke volume variation (SVV).

In other cases, bio-impedance based stroke volume variation (SVV) values and plethysmography based stroke volume variation (SVV) values are both actively calculated and compared by the processor 143. Depending on the difference between the two values, one or the other may be chosen to present as the stroke volume variation (SVV) to the user (e.g., via the display 149). Or, a mean of the two values may be determined and then presented as the stroke volume variation to the user. In some embodiments, a stroke volume variation (SVV) value is calculated as follows. The processor 143 calculates (within a particular respiratory cycle) a first provisional stroke volume variation value from two or more stroke volumes (SV) values calculated from the bio-impedance data obtained from at least two of the sensors (electrodes) 134. The processor 143 then calculates (using the same respiratory cycle) a second provisional stroke volume variation value from two or more stroke volumes obtained from the plethysmographic data obtained at least partially from the first optical sensor. The processor 143 then compares the first provisional stroke volume variation value with the second provisional stroke volume variation value, and determines a final stroke volume variation value. In some embodiments, the first provisional stroke volume variation value may be chosen because a) the necessary data is present and/or uncorrupted and/or undisturbed and b) it represents the preferred modality at the time (e.g., in one example, bio-impedance) through which a stroke volume variation value is desired. In some cases, the second provisional stroke volume variation value may be chosen because the necessary data is not present and/or is corrupted and/or disturbed.

In some embodiments, the processor may be configured so that, in the case that both the bio-impedance data and the plethysmographic data are usable, and the first provisional stroke volume variation value and second stroke volume variation value are not substantially different from one another (e.g., difference of less than 15%, or difference of less than 10% or difference of less than 5%) (or less than or equal to), a final stroke volume variation value is determined. For example, the final stroke volume variation value may be determined by taking a mean of the first provisional stroke volume variation value and the second provisional stroke volume variation value (one-half the sum of the two values). In some embodiments, the final stroke volume variation value may even be a value between the first provisional stroke volume variation value and the second provisional stroke volume variation value, without being the mean. For example, it may be a weighted value, favoring one of the two provisional values. For example, one-third of the quantity of two times the first provisional stroke volume variation value plus one time the second provisional stroke volume variation value.

In some embodiments, the processor 143 may be configured so that, in the case that both the bio-impedance data and the plethysmographic data are usable, and the first provisional stroke volume variation value and second provisional stroke volume variation value are not substantially different from one another (e.g., difference of less than 15%, or difference of less than 10% or difference of less than 5%) (or less than or equal to), a final stroke volume variation value is chosen to be one of the two provisional values (for example, the second provisional stroke volume variation value). For example, in one particular configuration, the processor 143 may be configured to use the stroke volume variation value obtained from the bio-impedance data, as long as the first provisional stroke volume variation value and second stroke volume variation value do not differ by more than 10%. It should be noted that, even if one of the first provisional stroke volume variation value and second provisional stroke volume variation value is not represented (in whole or in part) in the final stroke volume variation value, the final stroke volume variation value selection is nevertheless based in part on the second provisional stroke volume variation value as long as the second provisional stroke volume is used or assessed in the process leading up to the selection of the final stroke volume variation value.

In another possible configuration, the processor 143 may be configured to use the stroke volume variation value obtained from the bio-impedance data, as long as the first provisional stroke volume variation value and second stroke volume variation value do not differ by more than a threshold percentage (e.g., 10%), and to display no stroke volume variation value if the first provisional stroke volume variation value and second stroke volume variation value differ by more than the threshold percentage. In this case, the particular respiratory cycle would not be used and a subsequent respiratory cycle would be used for the next calculations.

In some embodiments, the user is able to control the selection criteria for choosing a stroke volume variation value via input via the interface 153.

These calculation and determination methodologies, as described, are also appropriate for use with the other embodiments described in the following FIGS. 8-19.

Figure 8:
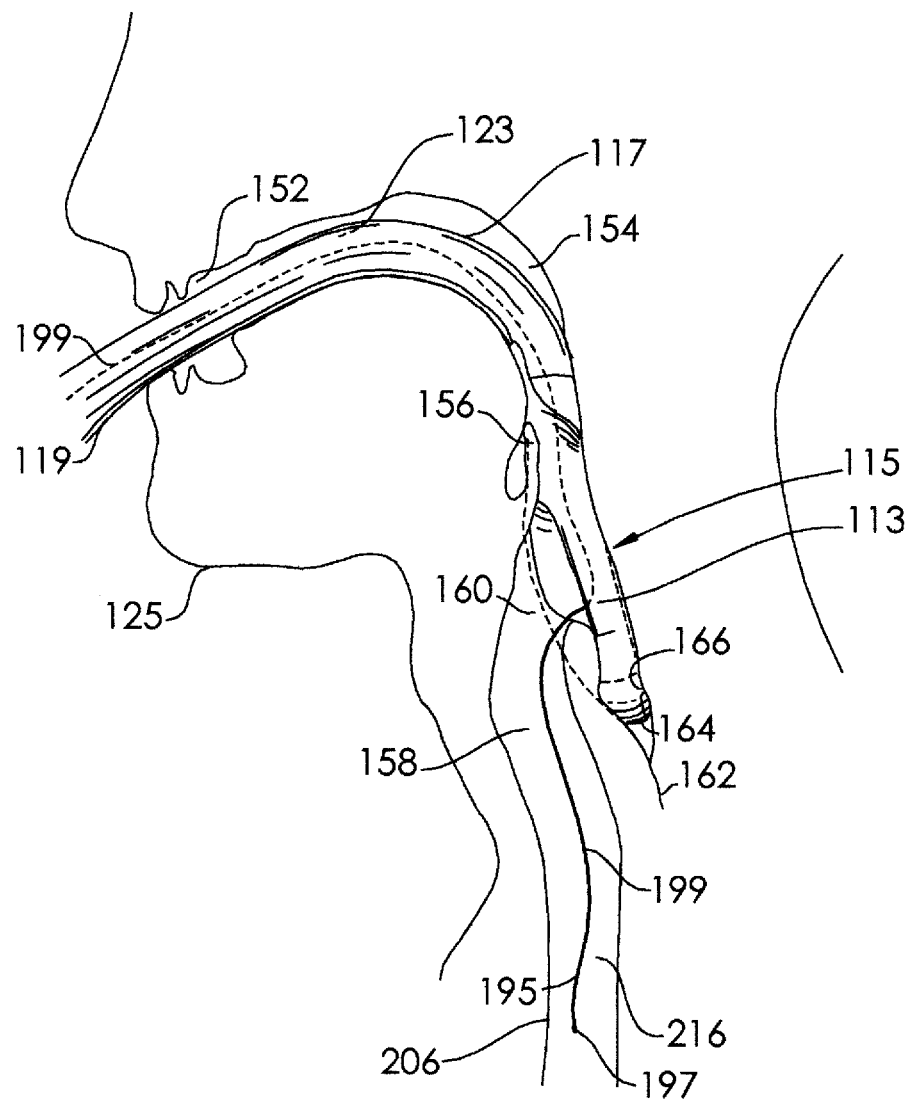
FIG. 8 is a partial sectional view of a system for cardiovascular sensing, according to another embodiment of the present disclosure.

In an alternative embodiment, one or more additional optical sensors 197 (e.g., a pulsed oximetry devices) (FIG. 8) may be separate from the LMA 115 and may be configured for placement in a remote location on the patient 125. For example, the optical sensor 197 may be placed within a trachea, or a bronchus, of the esophagus, as described in other embodiments of sensing devices described herein. FIG. 8 illustrates an optical sensor 197 secured to a distal end 195 of an elongate member 199 that is threaded through the passageway 123 of the respiratory tube 117 of the LMA 115. The optical sensor 197 is extended out through one of the holes 111A and into a lumen 216 of the trachea 206. The optical sensor 197 is positioned in spaced relation with tissue, for example, in a non-contact arrangement with an inner wall of the trachea 206 and configured to work by using reflectance methodology from an inner surface of the trachea 206. In some embodiments, the optical sensor 197 may be placed in or near a duct or organ.

Figure 10:
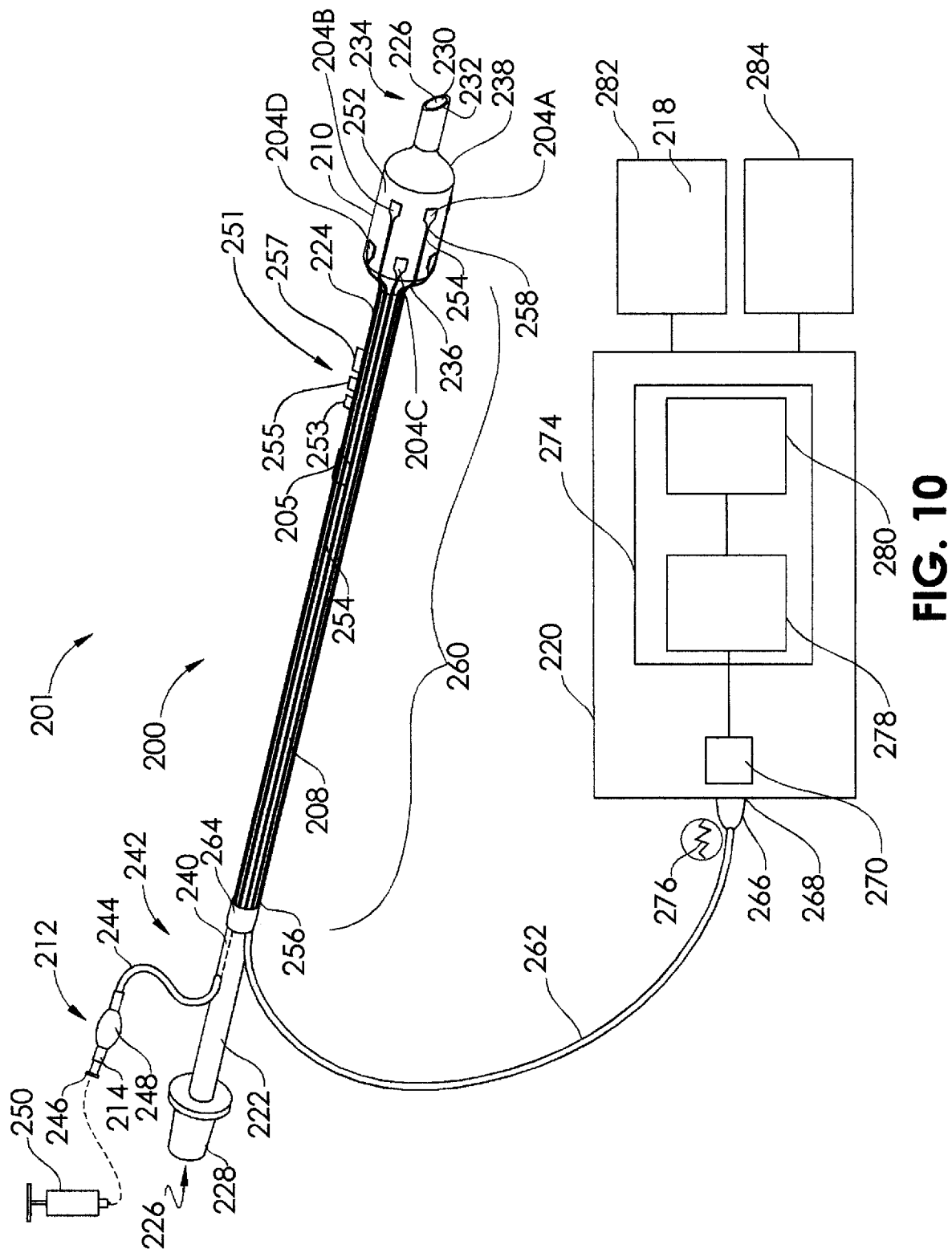
FIG. 10 is perspective view a system for cardiovascular sensing including a sensing device having an expandable member, according to an embodiment of the present disclosure.

FIG. 10 illustrates a system for measurement of cardiovascular parameters 201 comprising a sensing device 200 which is configured to be coupled to a console 220. The system for measurement of cardiovascular parameters 201 is configured to sense signals related to cardiovascular parameters of the heart. The sensing device 200 comprises an elongate member 208, which may comprise a shaft or catheter tubing. The elongate member 208 has a proximal end 222 and a distal end 224. The sensing device 200 as depicted in FIG. 10 is configured to serve as an endotracheal tube, and thus the sensing device 200 comprises a respiratory lumen 226 extending between a fitting 228, coupled to the proximal end 222 of the elongate member 208 and a port 230 adjacent the distal end 224 of the elongate member 208. The respiratory lumen 226 may be configured to allow the passage of a guidewire (not shown), which may be placed through the respiratory lumen 226 to aid in the delivery of the sensing device 200 within the body cavities of the subject, and which may be subsequently removed. At the port 230, the elongate member 208 may include a skive 232, or angled cut or formed tip, to aid in the tracking of the distal end 234 of the sensing device 200. The fitting 228 is configured to couple to a respiratory or other oxygen or air delivery apparatus, for delivering oxygen and other gases, which may in some cases include an anesthetic, through the respiratory lumen 226 and out the port 230 and into the patient's lungs, for example via the trachea and/or bronchi.

An actuation portion 210 having a proximal end 236 and a distal end 238 is carried by the distal end 224 of the elongate member 208, or may be actually formed from the distal end 224 of the elongate member 208. The actuation portion 210 may comprise an inflatable member, such as a balloon or cuff, or an otherwise expandable structure, and can be configured to have a low-profile state for placement into a body lumen or cavity and delivery within the body lumen or cavity (or within the lumen of a sheath or tube, including a catheter tube). The inflatable member and the elongate member 208 may comprise a polymer such as polyvinyl chloride (PVC) or polyethylene. The actuation portion 210 can also have an expanded state. If the actuation portion 210 is an inflatable member, then the expanded state may be achieved by inflating the actuation portion 210 (inflatable member) with a fluid, such as a gas or liquid. The fluid may include, for example, water, normal saline, air, nitrogen, or other inflation media. An inflation lumen 240 extends from a proximal location 242 to the actuation portion 210 (inflatable member) and is accessed at an interface 212, which may be coupled to the inflation lumen 240 via extension tubing 244. The interface 212 may comprise a luer fitting 246 configured to attach to a syringe or other type of inflation device 250. The interface 212 may include a valve 214, such as a luer-activated valve. The luer-activated valve may be configured to be in a closed (sealed) state when no inflation device is attached to the luer fitting 246, and may be configured to be in an open (unsealed) state when an inflation device is attached to the luer fitting 246. A pilot balloon 248 may be carried on the interface 212 to give tactile or visual feedback for a user to determine the extent of inflation of the inflatable member.

In FIG. 10, the actuation portion 210 is an inflatable member which carries one of more sensors 204 (204A, 204B, 204C, 204D) on its surface 252. Additionally, one or more shaft-based sensors 205 are carried on the elongate member 208. The total number of sensors 204 carried on the actuation portion and sensors 205 carried on the elongate member 208 may be varied in different embodiments. The one or more sensors 204 are secured to the surface 252 of the actuation portion 210 by adhesive or epoxy, or the one of more sensors 204 may be deposited, painted, coated, sprayed, sputtered, or otherwise attached or adhered to the surface 252. In some embodiments, the one or more sensors 204 may be applied to the surface 252 of the actuation portion 210 by use of a masking process described herein. In other embodiments, the one or more sensors 204 may be applied by a computer-controlled or robotic applicator which applies the sensor 204 in a computer-controlled pattern to the surface 252. In some embodiments, the one or more sensors 204, 205 are electrodes comprising an electrically conductive material, which may comprise silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 204, 205 under radiography or fluoroscopy.

One or more optical sensors 251, each comprising at least two light emitting sources 253, 255 and one light detector 257, are carried on the elongate member 208. As in system for measurement of cardiovascular parameters 100 of FIG. 4, the optical sensor 251 is configured to obtain plethysmographic data when it is positioned in spaced relation with tissue, for example, in a non-contact arrangement with an inner wall of a body lumen. Also, as in the system for measurement of cardiovascular parameters 100 of FIG. 4, the sensors 204 utilize bio-impedance to generate waveforms representative of the pulsatile flow of blood. However, because the actuation portion 210 is configured to be placed in the trachea, the adjacent area having significant pulsatile blood flow is the ascending aorta or central vasculature. The ascending aorta represents blood flow close to that of the cardiac output; Doppler methods often rely on the descending aorta for measurements of stroke volume, which does not include flow from the head and upper body portions.

The sensors 204, 205 are also used to obtain an electrocardiogram signal from the body of the patient to provide electrical timing information, as described in U.S. provisional application No. 62/159,912, filed May 11, 2015, and entitled "SYSTEMS AND METHODS FOR INTERNAL ECG ACQUISITION," and international publication number WO2016/179563, published on Nov. 10, 2016, and entitled "SYSTEMS AND METHODS FOR INTERNAL ECG ACQUISITION."

Each of the one or more sensors 204, 205 or one or more optical sensors 251 may be coupled to a conductor 254 having a proximal end 256 and a distal end 258. The one or more conductors 254 may be applied to the actuation portion 210 and the elongate member 208 by the same process with which the one or more sensors 204 are applied to the actuation portion 210. The one or more conductors 254 may be applied at the same time as the one or more sensors 204, 205 or may be applied before or after the application of the one or more sensors 204. In some embodiments, the one or more sensors 204, 205 are partially applied (e.g., a single layer or a first number of layers), the one or more conductors 254 are then applied, and then a final one or more layers are applied to complete the one or more sensors 204, 205. In some embodiments, a dielectric layer 260 is subsequently applied over the one or more conductors 254 after the application of the one or more conductors 254. A cable 262 is electrically coupled to the proximal ends 256 of the one or more conductors 254 (for example, with solder), and a covering or strain relief 264 may be secured over the area of connection. The covering or strain relief 264 may be a dielectric material, including polyimide, adhesive or epoxy, polyethylene or polyester shrink tubing or other similar materials or combinations thereof.

The cable 262 includes a connector 266 which is configured to be coupled to an input 268 of the console 220 and is configured to carry signals 276 from the one or more sensors 204 and optical sensor 251 to the console 220. Signals 276 entering the console 220 may in some embodiments represent several different sensors 204 (having been carried by several corresponding conductors 254). In some embodiments, the console 220 may include an analog-to-digital converter 270 through which the one or more signals 276 are converted. In some embodiments, the signals 276 may be multiplexed. The one or more signals 276 may enter a processor 274 provided by the console 220. The processor 274 may include one or more amplifiers 278 for amplifying the signal 276 and one or more filters 280 for filtering the signal 276. A display 282 is configured to display a resulting graphic representation 218. The graphic representation 218 may simply be a parameter value or a table of values, or may actually be a graph of data. The display 282 may be built in to the console 220 or may be separate. The display 282 may be directly connected to the console 220 or may be remote and communicate wirelessly. The console 220 may include an interface 284 which allows a user to control and/or communicate with the console 220 or the system for measurement of cardiovascular parameters 201 in general. The interface 284 may even allow a user to control or communicate with the sensing device 200, for example, if the sensing device 200 incorporates an internal microprocessor, which may be carried on a flex circuit. The interface 284 may be a touch screen, a keyboard, an audio communication system (e.g., voice-activated), and may incorporate a graphic user interface (GUI).

The system for measurement of cardiovascular parameters 201 described herein is useful to measure physiological functions/parameters in mammalian subjects, including stroke volume, cardiac output, and stroke volume variation. Once the actuation portion 210 is positioned and expanded, a current is injected into the subject's tissue through one of the electrodes (sensors 204, 205) serving as a current electrode, a voltage is established between the current electrode and the ground electrode (one of sensors 204, 205) so that a current flows through the tissue disposed between the current electrode and the ground electrode. With one or more sense electrodes (sensors 204), the voltages caused by the current flowing in the tissue are detected, wherein the voltages vary in accordance with changes in the bioelectrical impedance of the tissue.

Figure 11:
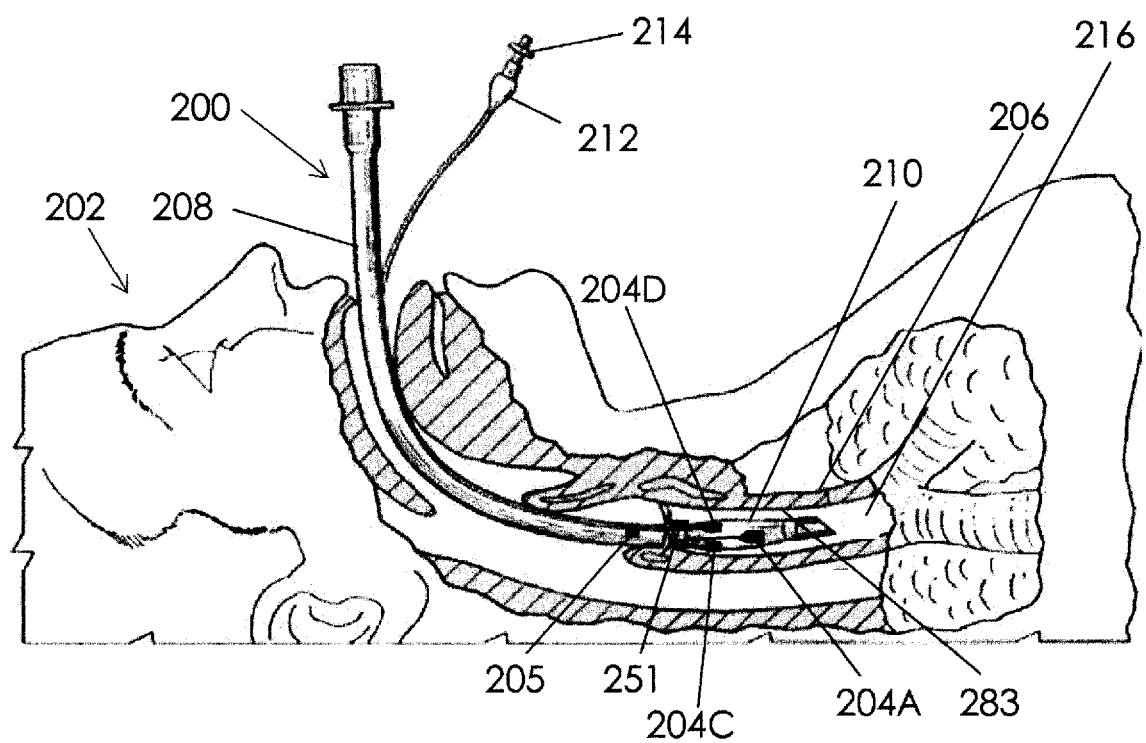
FIG. 11 is a partial sectional view of the sensing device of FIG. 10 placed within a trachea of a subject according to an embodiment of the present disclosure.
Figure 12:
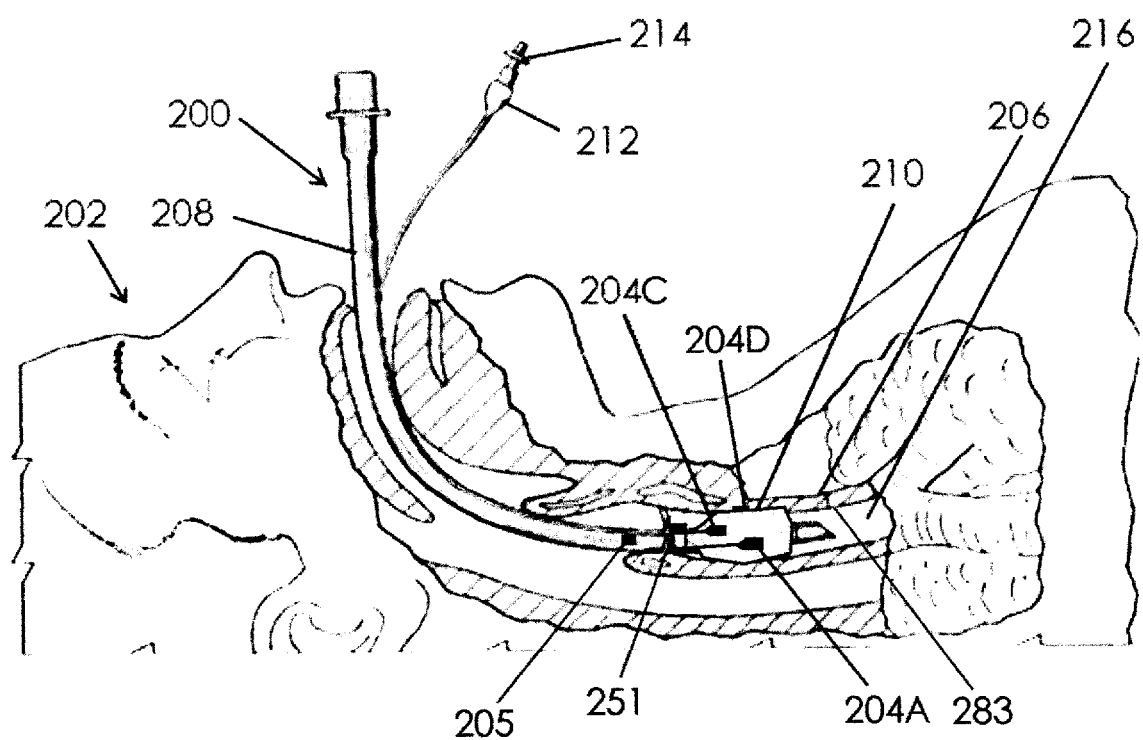
FIG. 12 is a partial sectional view of the sensing device of FIG. 10 having an actuation portion in an expanded state.

FIG. 11. Illustrates the sensing device 200 in place within a patient 202, such that the actuation portion 210 is within a lumen 216 of the trachea 206 while it its low-profile or deflated state. In use, a user inserts the sensing device into the patient's mouth and advances the actuation portion 210 into the trachea 206. By attaching an inflation device (e.g., syringe 250, FIG. 10) to the interface 212, the user may inflate the actuation portion 210 (e.g., balloon, cuff) (FIG. 12) such that the sensors 204 (e.g., electrodes) contact the interior wall 283 of the trachea 206. The valve 214 maintains the desired inflated pressure, and thus maintains the contact of the sensors 204 with the interior wall 283 of the trachea 206. Because the sensors 204 are contacting the soft tissue (e.g., mucosa) of the interior wall 283, an acceptable electrical contact is made without the need for coupling gel or liquid. The maintenance of pressure inside the actuation portion 210 assures that the electrical contact between the sensors 204 and the interior wall 283 is not interrupted. This is in contrast to traditional electrode pads that are carried by the skin that typically incorporate a coupling gel, and which nevertheless can be accidentally pulled off, scraped off or can fall off because of sweating or contamination (spilling, etc.) in the application area.

The optical sensor 251, when the actuation portion 210 is expanded within the trachea 206, is in a spaced (non-contact) relation with the interior wall 283 of the trachea 206, thus allowing for the reflectance of the optical radiation.

Figure 9:
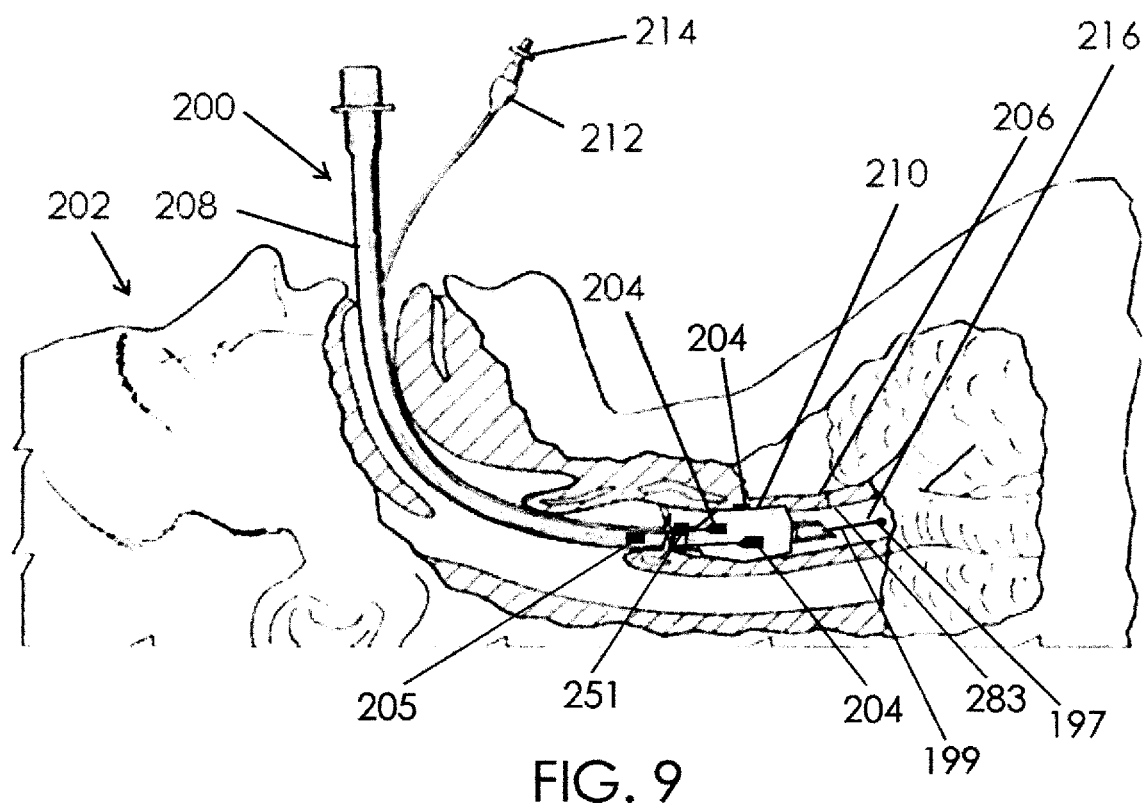
FIG. 9 is a partial sectional view of a system for cardiovascular sensing, according to another embodiment of the present disclosure.

In an alternative embodiment, one or more additional optical sensors 197 (e.g., a pulsed oximetry devices) (FIG. 9) may be separate from the sensing device 200 and may be configured for placement in a remote location on the patient 202. For example, the optical sensor 197 may be placed within a trachea. FIG. 9 illustrates an optical sensor 197 secured to a distal end of an elongate member 199 that is threaded through the respiratory lumen 226 of the elongate member 208 of the sensing device 200. The optical sensor 197 is extended out distally through the port 230 and into the lumen 216 of the trachea 206. The optical sensor 197 is positioned in spaced relation with tissue, for example, in a non-contact arrangement with an inner wall of the trachea 206 and configured to work by using reflectance methodology from an inner surface of the trachea 206. In some embodiments, the optical sensor 197 may be placed in or near a duct or organ.

Though the actuation portion 210 is configured to be expanded within the trachea 206, in alternative embodiments, the sensing device 200 may be placed inside the esophagus of a subject, and the actuation portion 210 expanded such that the sensors 204 contact an interior wall of the esophagus.

Figure 13:
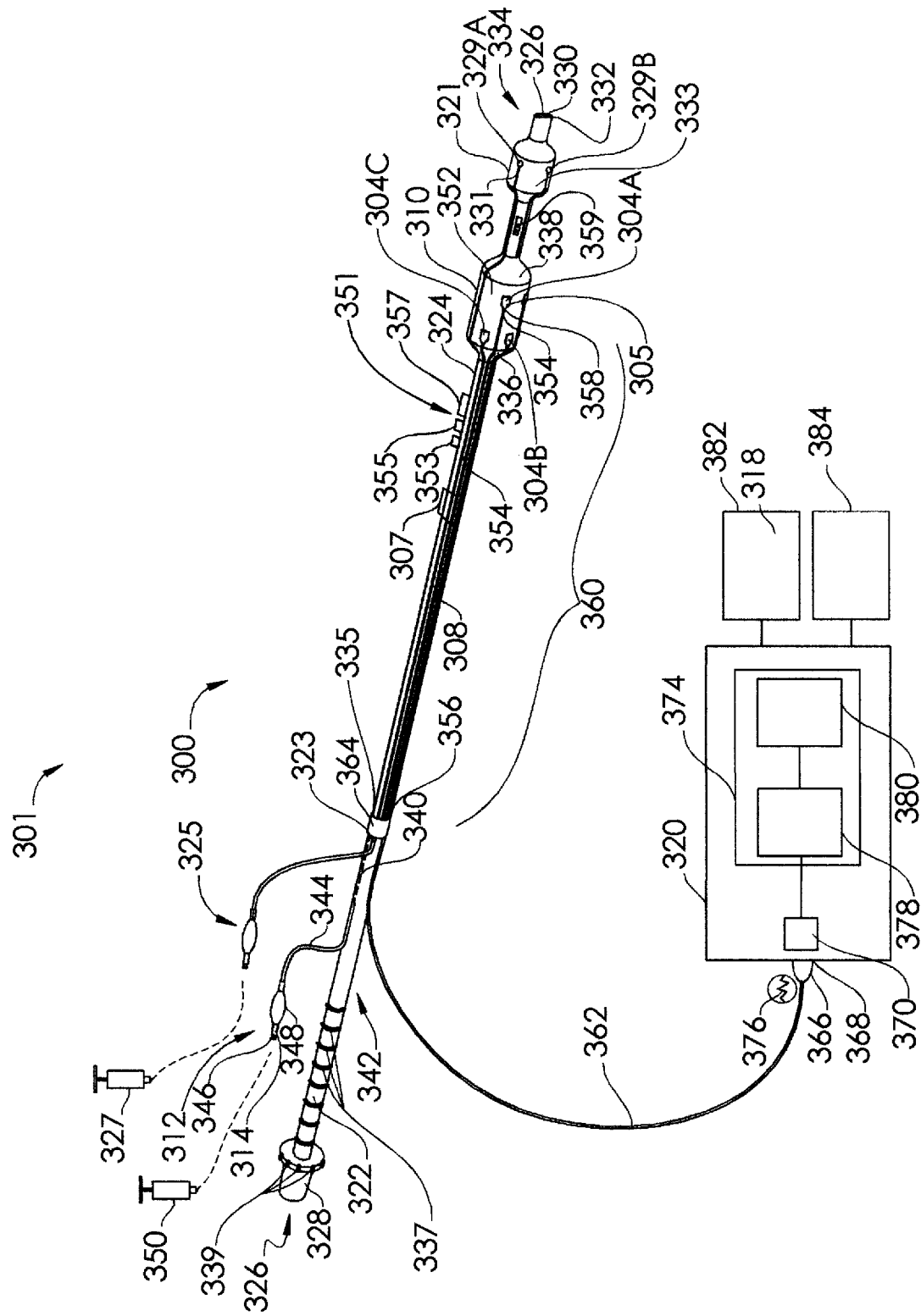
FIG. 13 is perspective view a system for cardiovascular sensing including a sensing device having two expandable members, according to an embodiment of the present disclosure.

FIG. 13 illustrates a system for measurement of cardiovascular parameters 301 comprising a sensing device 300 which is configured to be coupled to a console 320. The system for measurement of cardiovascular parameters 301 is configured to sense signals related to cardiovascular parameter of the heart. The sensing device 300 comprises an elongate member 308, which may comprise a shaft or catheter tubing. The elongate member 308 has a proximal end 322 and a distal end 324. The sensing device 300 as depicted in FIG. 13 is configured to serve as an endotracheal tube having sub-selective capability, and thus the sensing device 300 comprises a respiratory lumen 326 extending between a fitting 328, coupled to the proximal end 322 of the elongate member 308 and a port 330 adjacent the distal end 324 of the elongate member 308. The respiratory lumen 326 may be configured to allow the passage of a guidewire (not shown), which may be placed through the respiratory lumen 326 to aid in the delivery of the sensing device 300 within the body cavities of the subject, and which may be subsequently removed. At the port 330, the elongate member 308 may include a skive 332, or angled cut or form, to aid in the tracking of the distal end 334 of the sensing device 300. The fitting 328 is configured to couple to a respiratory or other oxygen or air delivery apparatus, for delivering oxygen and other gases, which may in some cases include an anesthetic, through the respiratory lumen 326 and out the port 330 in into the patient's lungs, for example via one or more bronchi.

Figure 15:
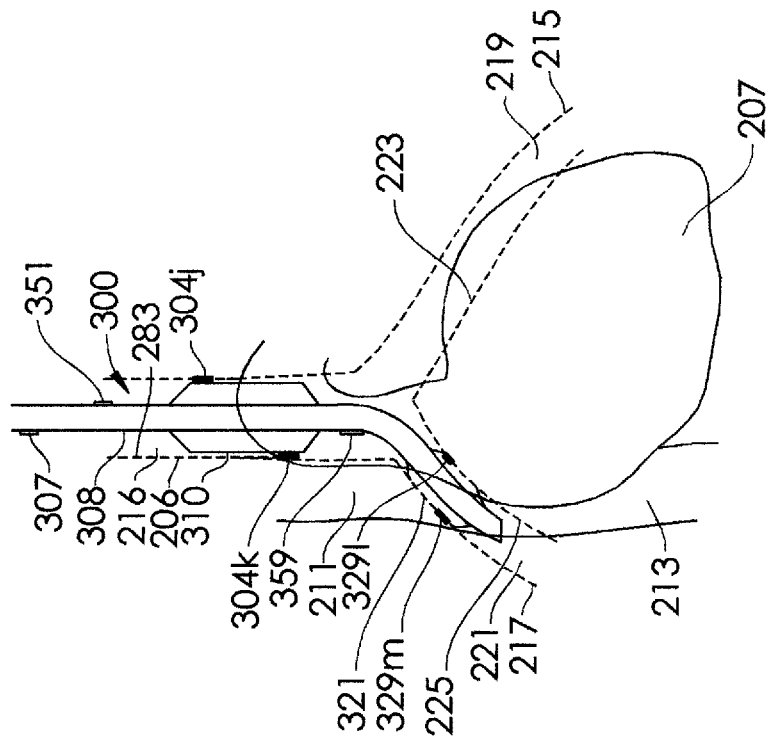
FIG. 15 is a view of the sensing device of FIG. 13 placed within the trachea and a bronchus of a subject, according to an embodiment of the disclosure.
Figure 14:
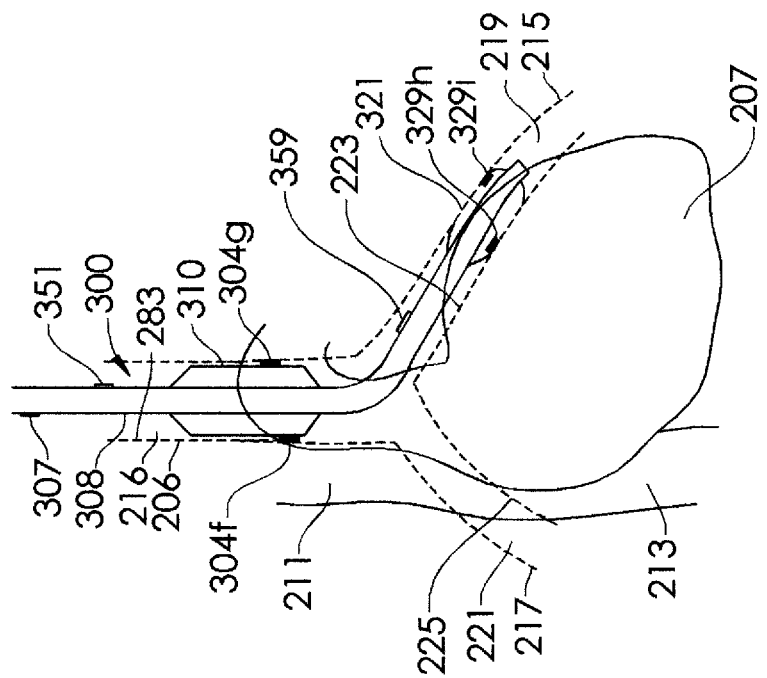
FIG. 14 is a view of the sensing device of FIG. 13 sensing device placed within the trachea and a bronchus of a subject, according to an embodiment of the present disclosure.

A first actuation portion 310 having a proximal end 336 and a distal end 338 is carried by the distal end 324 of the elongate member 308, or may be actually formed from the distal end 324 of the elongate member 308. The first actuation portion 310 may comprise an inflatable member, such as a balloon or cuff, or an otherwise expandable structure, and can be configured to have a low-profile state for placement into a body lumen or cavity and delivery within the body lumen or cavity (or within the lumen of a sheath or tube, including a catheter tube). The first actuation portion 310 can also have an expanded state. If the first actuation portion 310 is an inflatable member, then the expanded state may be achieved by inflating the first actuation portion 310 (inflatable member) with a fluid, such as a gas or liquid. The fluid may include, for example, water, normal saline, air, nitrogen, or other inflation media. An inflation lumen 340 extends from a proximal location 342 to the first actuation portion 310 (inflatable member) and is accessed at an interface 312, which may be coupled to the inflation lumen 340 via extension tubing 344. The interface 312 may comprise a luer fitting 346 configured to attach to a syringe or other type of inflation device 350. The interface 312 may include a valve 314, such as a luer-activated valve. The luer-activated valve may be configured to be in a closed (sealed) state when no inflation device is attached to the luer fitting 346, and may be configured to be in an open (unsealed) state when an inflation device is attached to the luer fitting 346. A pilot balloon 348 may be carried on the interface 312 to give tactile or visual feedback for a user to determine the extent of inflation of the inflatable member. Distal to the first actuation portion 310 is a second actuation portion 321 which is expandable. The second actuation portion 321 may be an inflatable member, such as a balloon or cuff, and may be expandable through the same inflation lumen 340 as the first actuation member 310, or, as illustrated in FIG. 13, may be independently expandable through a second inflation lumen 323 via a second interface 325, which may have similar features to the interface 312. For example, the second interface 325 may be inflated by an inflation device 327. In some embodiments, the first actuation member 310 may be configured to be inflated within a trachea 206 while the second actuation portion 321 may be configured to be inflated within a bronchus 215, 217 (FIGS. 14 and 15). In some embodiments, the first actuation portion 310 has a larger profile or diameter than the second actuation portion 321. For example, the diameter of the first actuation portion 310 may be between about 5 mm and about 30 mm, or between about 13 mm and about 27 mm, while the diameter of the second actuation portion 321 may be between about 4 mm and 20 mm, or between about 9 mm and about 18 mm.

In FIG. 13, the first actuation portion 310 is an inflatable member which carries one of more sensors 304 (304A, 304B, 304C) on its surface 352. Additionally, one or more shaft-based sensors 307 are carried on the elongate member 308. The total number of sensors 304 carried on the actuation portion and sensors 307 carried on the elongate member 308 may be varied in different embodiments. The one or more sensors 304 may be secured to the surface 352 of the first actuation portion 310 by adhesive or epoxy, or the one of more sensors 304 may be deposited, painted, coated, sprayed, sputtered, or otherwise attached or adhered to the surface 352. In some embodiments, the one or more sensors 304 may be applied to the surface 352 of the first actuation portion 310 by use of a masking process described herein. In other embodiments, the one or more sensors 304 may be applied by a computer-controlled or robotic applicator which applies the sensor 304 in a computer-controlled pattern to the surface 352. In some embodiments, the one or more sensors 304, 307 are electrodes comprising an electrically conductive material, which may comprise silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 304, 307 under radiography or fluoroscopy.

One or more optical sensors 351, each comprising at least two light emitting sources 353, 355 and one light detector 357, are carried on the elongate member 308. As in the system for measurement of cardiovascular parameters 201 of FIG. 10, the optical sensor 351 is configured to obtain plethysmographic data when it is positioned in spaced relation with tissue, for example, in a non-contact arrangement with an inner wall of a body lumen. Also, as in the system for measurement of cardiovascular parameters 201 of FIG. 10, the sensors 304 utilize bio-impedance to generate waveforms representative of the pulsatile flow of blood. Because the first actuation portion 310 is configured to be placed in the trachea, the adjacent area having significant pulsatile blood flow is the ascending aorta, which has the same benefits as described in relation to the system for measurement of cardiovascular parameters 201 of FIG. 10. A second optical sensor 359 may be carried on an intermediate portion of the elongate member extending between the first actuation portion 310 and the second actuation portion 321. Because the location of second optical sensor 359 when the first actuation portion 310 is expanded within the trachea 206 and the second actuation portion 321 is expanded within one of the bronchi 215, 217, the second optical sensor is configured to output a signal that at least partially provides an estimate of mixed venous oxygen saturation $SvO_2$ in the pulmonary artery of the subject.

The one or more sensors 304 each have a contact surface 305. Each of the one or more sensors 304 or one or more optical sensors 351 may be coupled to a conductor 354 having a proximal end 356 and a distal end 358. The one or more conductors 354 may be applied to the first actuation portion 310 and/or the elongate member 308 by the same process with which the one or more sensors 304 are applied to the first actuation portion 310. In some embodiments, the one or more sensors 304 and/or the one or more conductors 354 may be applied using methods described in U.S. Pat. No. 9,289,141 entitled "APPARATUS AND METHODS FOR THE MEASUREMENT OF CARDIAC OUTPUT," issued Mar. 22, 2016. The one or more conductors 354 may be applied at the same time as the one or more sensors 304 or may be applied before or after the application of the one or more sensors 304. In some embodiments, the one or more sensors 304 are partially applied (e.g., a single layer or a first number of layers), the one or more conductors 354 are then applied, and then a final one or more layers are applied to complete the one or more sensors 304. In some embodiments, a dielectric layer 360 is subsequently applied over the one or more conductors 354 after the application of the one or more conductors 354. One or more sensors 329 (329A, 329B) and one or more conductors 331 are applied to a surface 333 of the second actuation portion 321 by any of the methods described. The one or more conductors 331 may also be coated or otherwise covered by a dielectric material. The one or more conductors 331 may extend proximally within the interior of the elongate member 308, or may extend along with the one or more conductors 354 along an outer surface of the elongate member 308. A cable 362 is electrically coupled to the proximal ends 356 of the one or more conductors 354 and to proximal ends 335 of the one or more conductors 331 (for example, with solder), and a covering or strain relief 364 may be secured over the area of connection. The covering or strain relief 364 may be a dielectric material, including polyimide, adhesive or epoxy, polyethylene or polyester shrink tubing or other similar materials or combinations thereof.

The cable 362 includes a connector 366 which is configured to be coupled to an input 368 of the console 320 and is configured to carry signals 376 from the one or more sensors 304, one or more sensors 329, and one or more optical sensors 351, 359 to the console 320. Signals 376 entering the console 320 may in some embodiments represent several different sensors 304, 329 (having been carried by several corresponding conductors 354, 331). In some embodiments, the console 320 may include an analog-to-digital converter 370 through which the one or more signals 376 are converted. In some embodiments, the signals 376 may be multiplexed. The one or more signals 376 may enter a processor 374 provided by the console 320. The processor 374 in some embodiments includes one or more amplifiers 378 for amplifying the signal 376 and one or more filters 380 for filtering the signal 376. A display 382 is configured to display a resulting graphic representation 318. The graphic representation 218 may simply be a parameter value or a table of values, or may actually be a graph of data. The display 382 may be built in to the console 320 or may be separate. The display 382 may be directly connected to the console 320 or may be remote and communicate wirelessly. The console 320 may include an interface 384 which allows a user to control and/or communicate with the console 320 or the system for measurement of cardiovascular parameters 301 in general. The interface 384 may even allow a user to control or communicate with the sensing device 300, for example, if the sensing device 300 incorporates an internal microprocessor, which may be carried on a flex circuit. The interface 384 may be a touch screen, a keyboard, an audio communication system (e.g., voice-activated), and may incorporate a graphic user interface (GUI).

The system for measurement of cardiovascular parameters 301 described herein is useful to measure physiological functions/parameters in mammalian subjects, including stroke volume, cardiac output, and stroke volume variation. Once the actuation portion 310, 321 is positioned and expanded, a current is injected into the subject's tissue through one of the electrodes (sensors 304, 329, 307) serving as a current electrode, a voltage is established between the current electrode and the ground electrode (one of sensors 304, 329, 307) so that a current flows through the tissue disposed between the current electrode and the ground electrode. With one or more sense electrodes (sensors 304, 329), the voltages caused by the current flowing in the tissue are detected, wherein the voltages vary in accordance with changes in the bioelectrical impedance of the tissue.

A sensing device 300 is shown in FIG. 14 having sensors 304*f*, 304*g* disposed on its first actuation portion 310 which has been located and expanded within the lumen 216 of the trachea 206. In addition, sensors 329*h*, 329*i* are disposed on the second actuation portion 321 of the sensing device 300, and the second actuation portion 321 has been located and expanded within a lumen 219 of left bronchus 215. Each of the sensors 304*f*, 304*g* are contacting the interior wall 283 of the trachea 206. Each of the sensors 329*h*, 329*i* are contacting an interior wall 223 of the left bronchus 215.

A sensing device 300 is shown in FIG. 15 having sensors 304*j*, 304*k* disposed on its first actuation portion 310 which has been located and expanded within the lumen 216 of the trachea 206. In addition, sensors 329*l*, 329*m* are disposed on the second actuation portion 321 of the sensing device 300, and the second actuation portion 321 has been located and expanded within a lumen 221 of right bronchus 217. Each of the sensors 304*j*, 304*k* are contacting the interior wall 283 of the trachea 206. Each of the sensors 329*l*, 329*m* are contacting an interior wall 225 of the right bronchus 217. As can be seen with either in either of the positions of the sensing device 300 illustrated in FIGS. 14 and 15, moving the second actuation portion 321 either deeper into the bronchi 215, 217 or less deep (by collapsing/deflating the second actuation portion 321, advancing or retracting the sensing device 300, and re-expanding/inflating the second actuation portion 321) will change the location of the contact of the sensors 340, 329. Note relative locations of the heart 207, the superior vena cava 211, and the inferior vena cava 213. Returning to FIG. 13, depth markings 337 carried by the elongate member 308 allow precision placement and adjustment of the longitudinal location of the sensing device 300 and the first and second actuation portions 310, 321. The depth markings 337 may each be separated by 20 mm, 10 mm, 5 mm, or even 1 mm, or any distance between. Each depth marking 337 may be made similar to the other depth markings 337, or each may differ with the others, for specific identification. The depth markings 337 may be applied by any manner known in the art, such as pad printing, marking, colored shrink tubing, scoring, or other acceptable manners.

The sensors 304, 307 are also used to obtain an electrocardiogram signal from the body of the patient to provide electrical timing information, as described in U.S. provisional application No. 62/159,912, filed May 11, 2015, and entitled "SYSTEMS AND METHODS FOR INTERNAL ECG ACQUISITION," and international publication number WO2016/179563, published on Nov. 10, 2016, and entitled "SYSTEMS AND METHODS FOR INTERNAL ECG ACQUISITION."

The optical sensors 351, 359, when the first actuation portion 310 and second actuation portion 321 are expanded within the trachea 206 and a bronchus 215, 217, are each in a spaced (non-contact) relation with the interior wall 283 of the trachea 206 and the interior wall 223, 225 of the bronchus 215, 217, respectively, thus allowing for the reflectance of the optical radiation.

Additionally, by rotating the sensing device 300, the rotational orientation of the sensors 329*h*, 329*i*, 329*l*, 329*m* of the second actuation portion 321 and the sensors 304*f*, 304*g*, 304*j*, 304*k* of the first actuation portion 310 may also be changed, thus changing the portion of tissue they engage when the first actuation portion 310 and second actuation portion 321 are expanded. Circumferentially-arrayed markings 339 (FIG. 13) may be carried by the elongate member 308, or as illustrated, the fitting 338. The circumferentially-arrayed markings 339 may be applied by any manner known in the art, such as pad printing, marking, colored shrink tubing, scoring, or other acceptable manners. A temporary mark may be made on the patient's mouth (lip, etc.) as a landmark for comparing the location of the circumferentially-arrayed markings 339, or another piece of medical equipment nearby or other adjacent object may be used as a landmark. The markings 337, 339 and the adjustment methods described may also be used with the sensing device 200 of FIG. 10, or any of the other embodiments described herein.

Figure 16:
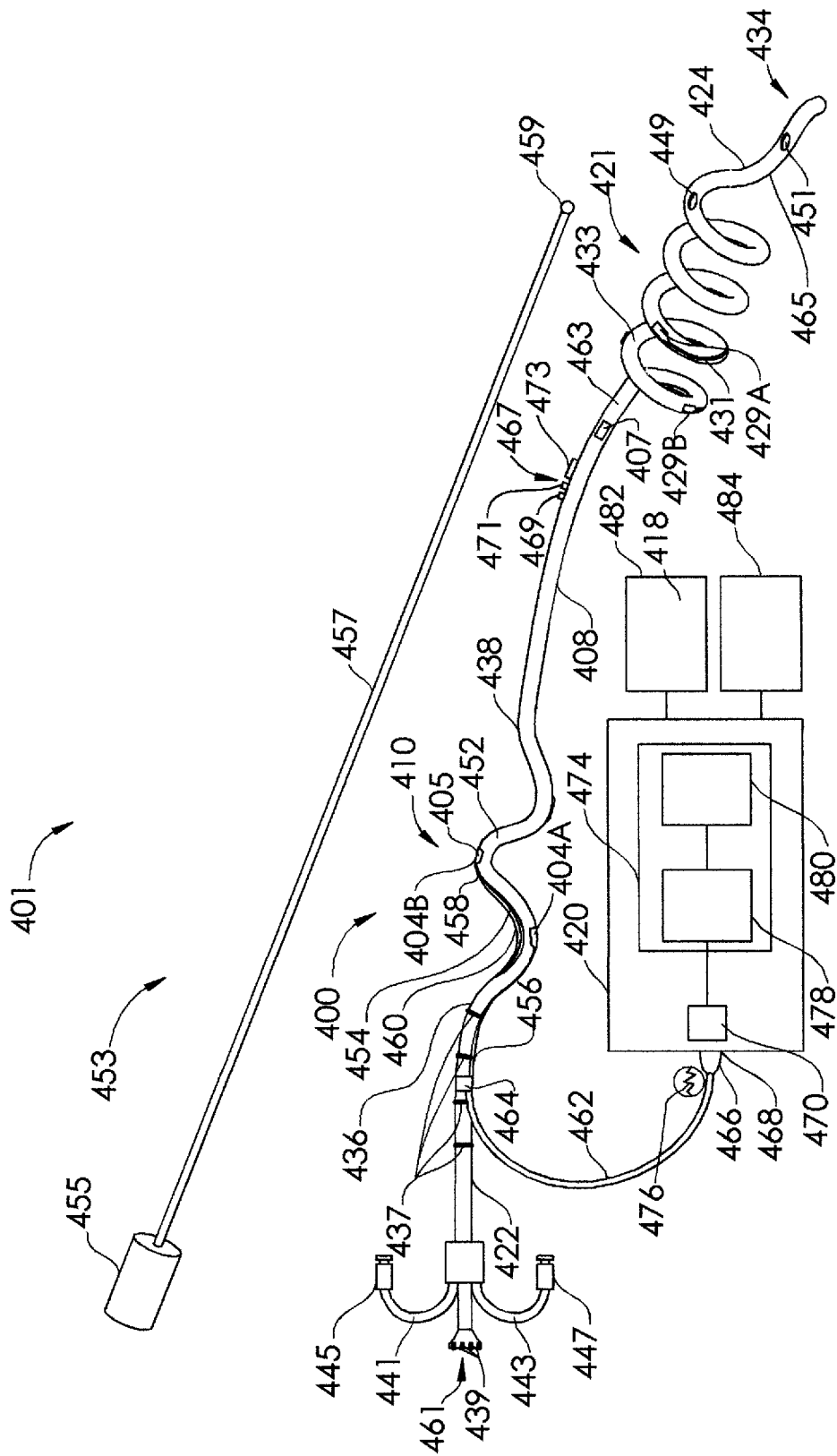
FIG. 16 is perspective view a system for cardiovascular sensing including a sensing device, according to an embodiment of the present disclosure.

FIG. 16 illustrates a system for measurement of cardiovascular parameters 401 comprising a sensing device 400 which is configured to be coupled to a console 420. The sensing system 401 is configured to sense signals related to cardiovascular parameters of the heart. The sensing device 400 comprises an elongate member 408, which may comprise a shaft or catheter tubing. The elongate member 408 has a proximal end 422 and a distal end 424. The sensing device 400 as depicted in FIG. 16 is configured to serve as a nasogastric tube (NG tube), and thus the sensing device 400 comprises one or more lumens 441, 443 extending between one or more fittings 445, 447 coupled to the proximal end 422 of the elongate member 408 and extending through the elongate member until terminating at one or more ports 449, 451 adjacent the distal end 424 of the elongate member 408. One of the ports 449, 451 may be configured for delivery of one or more medicants or for delivery of other fluids (e.g., normal saline) or for delivery of enteral feeding solutions. The ports 449, 451 may be located for direct delivery of the fluids into the stomach, but in alternative embodiments, the sensing device may be configured to allow at least one of the ports 449, 451 to be located in the duodenum or jejunum for direct delivery. In some cases, the port 449, 451 may be located in the distal esophagus. In some embodiments, one of the lumens 441, 443 may be dedicated to fluid delivery while the other lumen 441, 443 is dedicated to suction or lavage of internal contents, for example, stomach contents. In some embodiment, both of the lumens 441, 443 are capable of both delivery and suction or lavage. In some embodiments, the fittings 445, 447 comprises luer fittings, configured to couple to luer fittings of various delivery or suction devices.

Figure 17:
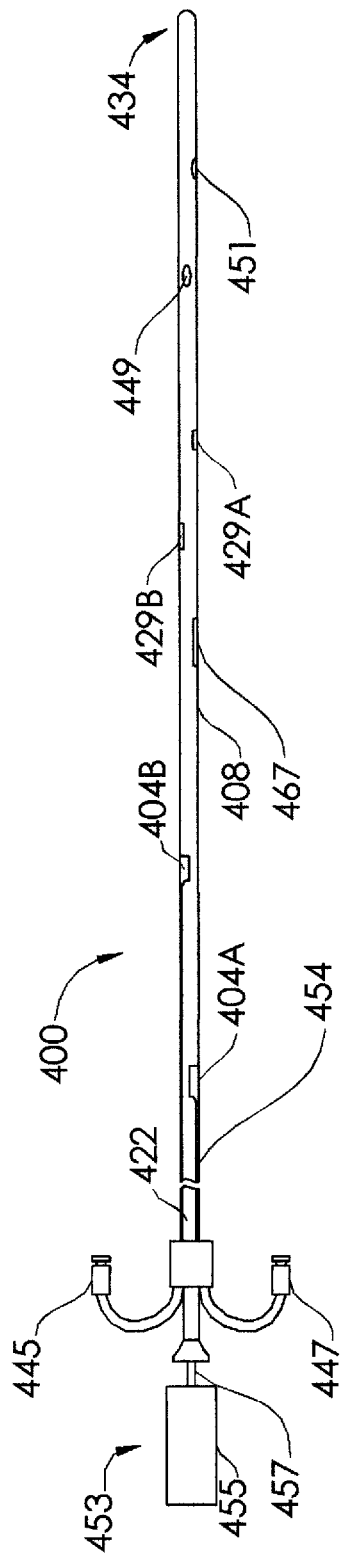
FIG. 17 is an elevation view of a sensing device of the system of FIG. 16 in a low-profile state.

A first actuation portion 410 having a proximal end 436 and a distal end 438 is carried by the elongate member 408. As illustrated in FIG. 16, the first actuation portion 410 in this particular embodiment comprises a secondary shape having an enlarged profile (in comparison to the diameter of the elongate member 408 shaft). The secondary shape is illustrated in FIG. 16 as a serpentine shape or S-shape formed directly in the elongate member 408. The shape may be formed by heat forming of a thermoplastic tubing. A stylet 453 having a proximal hub 455 and an elongate body 457 having a rounded or otherwise blunt tip 459 is configured to be placed down a central lumen 461 of the elongate member 408 of the sensing device 400. FIG. 17 illustrates the sensing device 400 with the elongate body 457 of the stylet 453 inserted within the central lumen 461, causing the first actuation portion 410 to assume a linear or substantially linear orientation, to aid in delivery or movement within a body cavity or lumen. When the sensing device 400 has been delivered to a desired location in the body lumen, for example, the esophagus and stomach, the elongate body 457 of the stylet 453 may be retracted or completely removed from the central lumen 461 of the sensing device 400, to allow the first actuation portion 410 to assume its secondary shape having an enlarged profile. In other embodiments, the elongate member 408 may comprise a shape memory polymer having shape memory which allows the first actuation portion 410 to achieve its desired secondary shape by contact with a patient's body temperature, or by introduction of a fluid having an increased temperature (e.g., 42° C.) around the elongate member 408. In another alternative embodiment, a shaped shape-memory alloy (e.g., Nitinol) resides within the elongate member 408 and causes the elongate member 408 to change shape at the first actuation portion 410 and/or the second actuation portion 421 when exposed to an elevated temperature (e.g., body temperature or an increased temperature, such as a temperature up to 42° C.). Alternatively, the first actuation portion 410 may be replaced by an inflatable member, such as a balloon or cuff such as those described in the embodiments of FIGS. 10 and 13. In general, the first actuation portion 410 comprises an expandable structure, and can be configured to have a low-profile state for placement into a body lumen or cavity and delivery within the body lumen or cavity (or within the lumen of a sheath or tube, including a catheter tube). As described, the first actuation portion 410 can also have an expanded state.

Distal to the first actuation portion 410 is a second actuation portion 421 having a proximal end 463 and a distal end 465. The second actuation portion 421 is expandable and comprises a low-profile state (FIG. 17) which may be achieved by placement of the elongate body 457 of the stylet 453 through the central lumen 461, and an expanded state (FIG. 16) which may be achieved by removal or retraction of the elongate body 457 of the stylet 453 from the central lumen 461. The secondary shape is illustrated in FIG. 16 as a spiral or helical shape formed directly in the elongate member 408. Any of the forming materials or methods used in relation to the first actuation portion 410 may also be used in relation to the second actuation portion 421. In some embodiments, the first actuation member 410 may be configured to be expanded within the esophagus while the second actuation portion 421 may be configured to be expanded within the esophagus at a location distal to the first actuation member 410. In some embodiments, the first actuation portion 410 has a smaller profile or diameter than the second actuation portion 421. For example, the (expanded) diameter of the first actuation portion 410 may be between about 15 mm and about 30 mm, or between about 20 mm and about 27 mm, while the (expanded) diameter of the second actuation portion 421 may be between about 25 mm and 40 mm, or between about 30 mm and about 37 mm. In some embodiments, both of the actuation portions 410, 421 may be spiral or helical. In some embodiments, both of the actuation portions 410, 421 may be serpentine or S-shaped. In some embodiments, the first actuation portion 410 may be spiral or helical and the second actuation portion 421 may be serpentine or S-shaped. Other three-dimensional or two-dimensional shapes may be used. In some embodiments, there may only be a single actuation portion, or in other embodiments, there may be three of more actuation portions. Though the ports 449, 451 are shown adjacent a distal end 434 of the sensing device 400, one or more ports 449, 451 may be located some distance proximal to the distal end 434, and in some embodiments proximal to the second actuation portion 421, and in some embodiments, even proximal to the first actuation portion 410. Markings 437, 439 can be utilized in the sensing device 400 as described in relation to the sensing device 300 of FIG. 13.

In FIG. 16, the first actuation portion 410 carries one of more sensors 404 (404A, 404B) on its outwardly-extending surfaces 452, such that the one or more sensors 404 are directed against an interior wall of the esophagus (or other body lumen) when the first actuation portion 410 is in its expanded state. Additionally, one or more shaft-based sensors 407 are carried on the elongate member 408. The total number of sensors 404 carried on the actuation portion and sensors 407 carried on the elongate member 408 may be varied in different embodiments. The one or more sensors 404 may be secured to the surface 452 of the first actuation portion 410 by adhesive or epoxy, or the one of more sensors 404 may be deposited, painted, coated, sprayed, sputtered, or otherwise attached or adhered to the surface 452. In some embodiments, the one or more sensors 404 may be applied to the surface 452 of the first actuation portion 410 by use of a masking process described herein. In other embodiments, the one or more sensors 404 may be applied by a computer-controlled or robotic applicator which applies the sensor 404 in a computer-controlled pattern to the surface 452. In some embodiments, the one or more sensors 404, 407 are electrodes comprising an electrically conductive material, which may comprises silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 404, 407 under radiography or fluoroscopy.

One or more optical sensors 467, each comprising at least two light emitting sources 469, 471 and one light detector 473, are carried on the elongate member 408. The optical sensor 467 is configured to obtain plethysmographic data when it is positioned in spaced relation with tissue, for example, in a non-contact arrangement with an inner wall of a body lumen. Also, the sensors 404, 429 utilize bioimpedance to generate waveforms representative of the pulsatile flow of blood. Because the actuation portion 410 is configured to be placed in the esophagus, the adjacent area having significant pulsatile blood flow is the ascending aorta.

The sensors 404, 407, 429 are also used to obtain an electrocardiogram signal from the body of the patient to provide electrical timing information, as described in U.S. provisional application No. 62/159,912, filed May 11, 2015, and entitled "SYSTEMS AND METHODS FOR INTERNAL ECG ACQUISITION," and international publication number WO2016/179563, published on Nov. 10, 2016, and entitled "SYSTEMS AND METHODS FOR INTERNAL ECG ACQUISITION."

The one or more sensors 404 each have a contact surface 405. Each of the one or more sensors 404, 429 or the one or more optical sensors 467 may be coupled to a conductor 454 having a proximal end 456 and a distal end 458. The one or more conductors 454 may be applied to the first actuation portion 410 and/or the elongate member 408 by the same process with which the one or more sensors 404 are applied to the first actuation portion 410. In some embodiments, the one or more sensors 404 and/or the one or more conductors 454 may be applied using methods described in U.S. Pat. No. 9,289,141 entitled "APPARATUS AND METHODS FOR THE MEASUREMENT OF CARDIAC OUTPUT," issued Mar. 22, 2016.

The one or more conductors 454 may be applied at the same time as the one or more sensors 404 or may be applied before or after the application of the one or more sensors 404. In some embodiments, the one or more sensors 404 are partially applied (e.g., a single layer or a first number of layers), the one or more conductors 454 are then applied, and then a final one or more layers are applied to complete the one or more sensors 404. In some embodiments, a dielectric layer 460 is subsequently applied over the one or more conductors 454 after the application of the one or more conductors 454. One or more sensors 429 (429A, 429B) and one or more conductors 431 are applied to outwardly-extending surfaces 433 of the second actuation portion 421 by any of the methods described. The one or more conductors 431 may also be coated or otherwise covered by a dielectric material. The one or more conductors 431 may extend proximally within the interior of the elongate member 408, or may extend along with the one or more conductors 454 along an outer surface of the elongate member 408. The one or more conductors 454 may also extend within the interior of the elongate member 408. A cable 462 is electrically coupled to the proximal ends 456 of the one or more conductors 454 and to proximal ends of the one or more conductors 431 (for example, with solder), and a covering or strain relief 464 may be secured over the area of connection. The covering or strain relief 464 may be a dielectric material, including polyimide, adhesive or epoxy, polyethylene or polyester shrink tubing or other similar materials or combinations thereof.

The cable 462 includes a connector 466 which is configured to be coupled to an input 468 of the console 420 and is configured to carry signals 476 from the one or more sensors 404, one or more sensors 429, and the one or more optical sensors 467 to the console 420. Signals 476 entering the console 420 may in some embodiments represent several different sensors 404, 429 (having been carried by several corresponding conductors 454, 431). In some embodiments, the console 420 may include an analog-to-digital converter 470 through which the one or more signals 476 are converted. In some embodiments, the signals 276 may be multiplexed. The one or more signals 476 may enter a processor 474 provided by the console 420. The processor 474 in some embodiments includes one or more amplifiers 478 for amplifying the signal 476 and one or more filters 480 for filtering the signal 476. A display 482 is configured to display a resulting graphic representation 418. The graphic representation 418 may simply be a parameter value or a table of values, or may actually be a graph of data. The display 482 may be built in to the console 420 or may be separate. The display 482 may be directly connected to the console 420 or may be remote and communicate wirelessly. The console 420 may include an interface 484 which allows a user to control and/or communicate with the console 420 or the system for measurement of cardiovascular parameters 401 in general. The interface may even allow a user to control or communicate with the sensing device 400, for example, if the sensing device 400 incorporates an internal microprocessor, which may be carried on a flex circuit. The interface 484 may be a touch screen, a keyboard, an audio communication system (e.g., voice-activated), and may incorporate a graphic user interface (GUI).

The system for measurement of cardiovascular parameters 401 described herein is useful to measure physiological functions/parameters in mammalian subjects, including stroke volume, cardiac output, and stroke volume variation. Once the actuation portion 410, 421 is positioned and expanded, a current is injected into the subject's tissue through one of the electrodes (sensors 404, 429, 407) serving as a current electrode, a voltage is established between the current electrode and the ground electrode (one of sensors 404, 429, 407) so that a current flows through the tissue disposed between the current electrode and the ground electrode. With one or more sense electrodes (sensors 404, 429), the voltages caused by the current flowing in the tissue are detected, wherein the voltages vary in accordance with changes in the bioelectrical impedance of the tissue.

Figure 18:
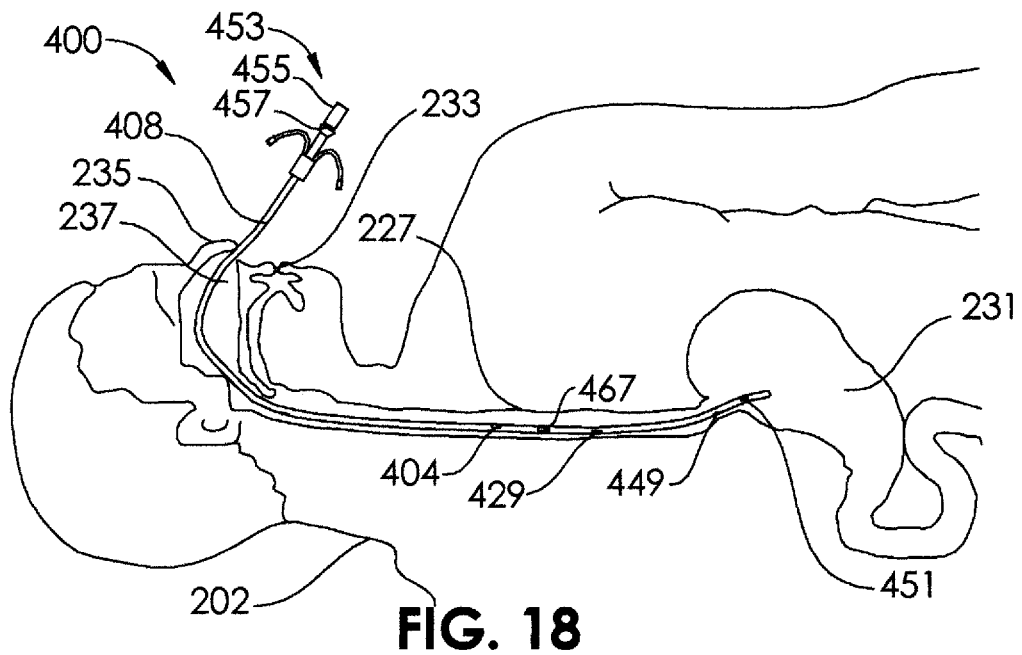
FIG. 18 is a partial sectional view of the sensing device of FIG. 16 within an esophagus of a subject in a low-profile state, according to an embodiment of the present disclosure.
Figure 19:
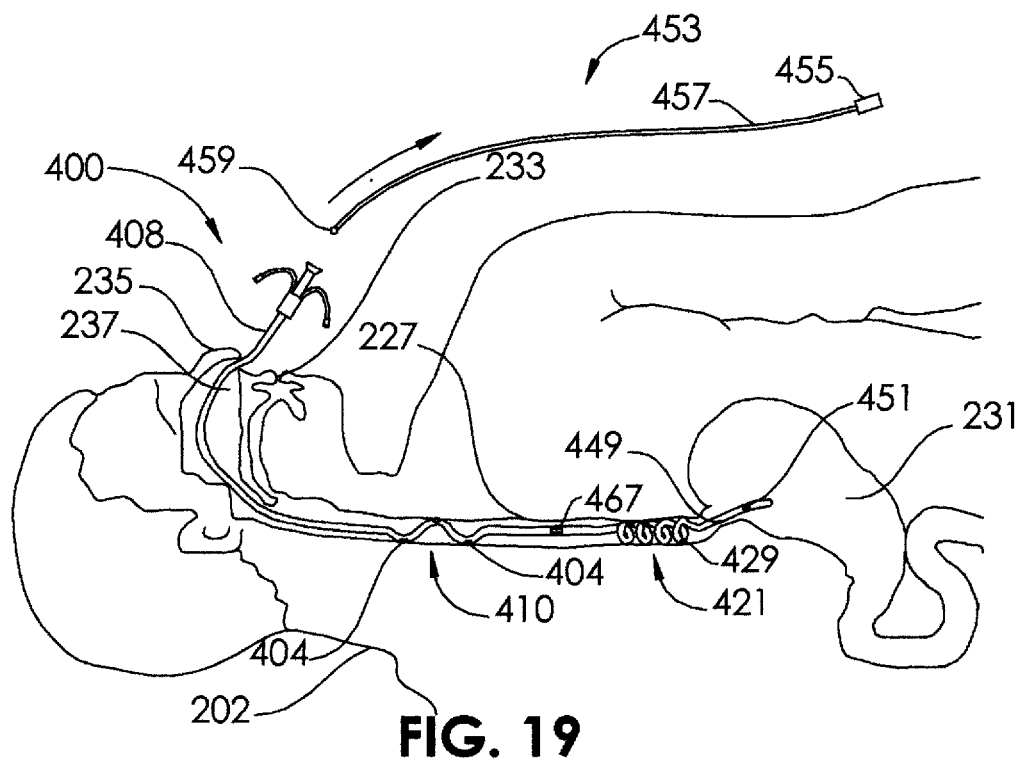
FIG. 19 is a partial sectional view of the sensing device of FIG. 16 within an esophagus of a subject in an expanded state, according to an embodiment of the present disclosure.

A sensing device 400 is shown in FIG. 18 with the stylet 453 inserted inside the elongate member 408 and being delivered through the nasal cavity 237 of the nose 235 of a patient 202 and into the esophagus 227. The mouth 233 is shown as a reference point. In FIG. 19, the stylet 453 is removed from the sensing device 400 and the elongate member 408 is adjusted as necessary so that the first actuation portion 410 and second actuation portion 421 assume their secondary expanded states in their desired locations. The sensors 404, 429 are applied against interior wall portions of the esophagus 227 by the first actuation portion 410 and second actuation portion 421. Port 451 has been placed into the interior of the stomach 231 for fluid delivery, suction, lavage, or other procedural purposes.

The optical sensor 467, when the actuation portion 410 is expanded within the esophagus 227, is in a spaced (non-contact) relation with the interior wall of the esophagus, thus allowing for the reflectance of the optical radiation.

A process for adding functionality to medical devices made of flexible plastic materials a process was developed to print an electrically conductive flexible electronic circuit on inflatable cuffs, balloons, sleeves or membranes. This process utilizes multidimensional measurement and imaging to establish a specific print pattern program of the device to allow for printing on inconsistent surfaces. Inconsistent surfaces may include folded surfaces, thin surfaces, stretchable surfaces, complex three-dimensional surfaces, uneven surfaces, and even partially or fully overlapping surfaces. The nature of disposable plastic devices that have expandable portions, including those having inflatable portions, is that the dimensions of the surface of the inflatable portions vary due to material inconsistencies, wall thicknesses and inflation pressures. An "intelligent" printing system has been used to adapt to these variations and/or inconsistencies to keep the deposited circuit consistent in dimensions and properties.

As an alternative, an apparatus and method are presented herein for printing and/or depositing and/or applying an electrical circuit using a machine that may be preprogrammed, but which does not require customization of the program for each device. This is accomplished by constraining the inflatable portion within a mask/fixture that has a precisely defined internal diameter. This mask comprises a material that is sufficiently rigid to allow for maintaining that internal diameter when the inflatable material is inflated into contact with the inner surface. The mask may comprise such materials as plastics (Delrin, PEEK, PTFE) or metals (Stainless Steel). The mask has the necessary openings cut out from its surface to allow for a printer or other applicator to deposit/apply the material on the constrained balloon, or inflatable portion, while at a known distance. In some embodiments, the balloon or inflatable portion may be inflated to a desired elevated pressure during the deposition. In some embodiments, this pressure may be adjusted in order to optimize the amount of masking. Alternatively, the "conductive ink" can be (without limitation) sprayed, atomized, painted, sputtered, or vapor deposited on the material exposed by the cut outs to form the circuit. After placement of the conductive tracings, a dielectric layer may be applied over a portion of the conductive tracings, for example, over all except any portions that are to be used as electrodes.

Examples of conductive tracings are described in U.S. provisional application No. 62/158,504, filed May 7, 2015, and entitled "IMPROVED FLEXIBLE ELECTRIC CIRCUIT ON FLEXIBLE MEMBRANES," international publication number WO2016/179563, published on Nov. 10, 2016, and entitled "SYSTEMS AND METHODS FOR INTERNAL ECG ACQUISITION," and U.S. Pat. No. 9,289,141, issued on Mar. 22, 2016, and entitled "APPARATUS AND METHODS FOR THE MEASUREMENT OF CARDIAC OUTPUT."

In any of the embodiments of the sensing devices 115, 200, 300, 400 described herein, additional sensors 134, 204, 304, 329, 404, 429 may be carried on the cuff/actuation portion 113, 210, 310, 321, 410, 421 to provide additional electrodes/measurement sites. In some embodiments, three or more, or even four or more, or five or more, sensors 134, 204, 304, 329, 404, 429 may be carried on a single cuff/actuation portion 113, 210, 310, 321, 410, 421.

In alternative embodiments of any of the sensing devices 115, 200, 300, 400 described herein, one or more additional optical sensors may be carried on the cuff/actuation portion 113, 210, 310, 321, 410, 421 on a particular surface that is not configured to contact an internal surface of a body lumen when the cuff/actuation portion 113, 210, 310, 321, 410, 421 is expanded. For example, the one or more additional optical sensors may be carried on a rear surface, away from the contact point(s), thus allowing for the reflectance of the optical radiation from the internal surface of the body lumen.

Though the systems for measurement of cardiovascular parameters 100, 201, 301, 401 described herein do not necessarily include an arterial catheter 6 (FIG. 1), an external cuff 42, 43 (FIG. 3), or a finger-mounted optical sensor 22 (FIG. 2), other embodiments are contemplated when additionally add one or more of these elements, or another related element (pulmonary artery catheter 4, FIG. 1, or an external cuff, such as an arm-placed cuff). In some embodiments, data obtained from any one of these other elements may also be used in the calculation of the stroke volume variation (SVV). For example, a first provisional stroke volume variation value may be taken from bio-impedance data (from one or more sensor 134, 204, 304, 329, 404, 429) and a second provisional stroke volume variation value may be taken from data obtained by one of the other elements (e.g., an external cuff).

Devices that may incorporate the improvements taught herein include standard or modified endo-tracheal tubes, nasogastric (NG) tubes, laryngeal masks, gastric lavage tubes, gastric aspiration tubes, gastric decompression tubes, Ewald orogastric tubes, Lavacutor® orogastric tubes, Edlich orogastric tubes, sump tubes, Salem tubes, Levin tubes, gastric suction/feeding tubes, Moss Mark IV nasal tubes, Dobbhoff nasojejunal feeding and gastric decompression tubes, nasointestinal tubes, Miller-Abbott tubes, or Sengstaken-Blakemore tubes. Any of these devices may include any of the embodiments of the sensing devices 115, 200, 300, 400 incorporated therein.

Other embodiments are envisioned which do not incorporate the application of a conductive material, but rather a non-conductive material. Some embodiments may incorporate resistive materials, which may be used to construct a device for delivering thermal therapy to a portion of the body. Some embodiments may incorporate a radiopaque material.

While embodiments have been shown and described, various modifications may be made without departing from the scope of the inventive concepts disclosed herein.

What is claimed is:

1. A method for measuring a stroke volume variation of a subject comprising:
providing a system for measuring cardiovascular data comprising:
an elongate member having a distal end configured for insertion within a body lumen of a subject and a proximal end configured to extend from the subject;
a first expandable member carried by the elongate member, the first expandable member having a collapsed state and an expanded state and configured to be movable between the collapsed state and the expanded state by adjustment initiated externally of the subject;
first and second sensors disposed on a surface of the first expandable member and configured to contact a wall of the body lumen of the subject when the first expandable member is in its expanded state; and
a first optical sensor located at a first location in relation to the distal end of the elongate member and configured for obtaining photoplethysmographic data;
inserting the distal end of the elongate member into a lumen or duct of a patient;
expanding the first expandable member such that the first and second sensors contact an internal surface of the patient;
obtaining data from at least the first and second sensors to calculate two or more stroke volumes (SV) of the patient;
obtaining photoplethysmographic data from the patient from the first optical sensor; and
calculating a stroke volume variation (SVV) of the patient based at least in part on the data obtained from the first and second sensors and the photoplethysmographic data obtained from the first optical sensor, wherein no data derived from intra-arterial blood pressure measurement is used in the calculation.

2. The method of claim 1, wherein the system further comprises a third sensor, the third sensor carried by the elongate member.

3. The method of claim 2, further comprising:
calculating a heart rate from one or both of: (a) the photoplethysmographic data obtained from the first optical sensor and/or (b) blood flow information from the data obtained by the first and second sensors and from data obtained from the third sensor.

4. The method of claim 2, further comprising:
calculating Sp02 from one or both of: (a) the photoplethysmographic data obtained from the first optical sensor and/or (b) blood flow information from the data obtained by the first and second sensors and from data obtained from the third sensor.

5. The method of claim 1, wherein the first optical sensor is remotely located from the elongate member.

6. The method of claim 1, wherein stroke volume variation (SVV) is governed by the following equation:

$$SVV = \frac{SV_{max} - SV_{min}}{SV_{mean}}$$

where $SV_{max}$ is a maximum stroke volume, $SV_{min}$ is a minimum stroke volume, and $SV_{mean}$ is a mean stroke volume of the two or more stroke volumes (SV), over a respiratory cycle.

7. The method of claim 1, wherein expanding the first expandable member comprises causing the first and second sensors to contact tissue in proximity to the larynx of the patient.

8. The method of claim 7, wherein obtaining data from at least the first and second sensors comprises obtaining data related to blood flow in one or more carotid arteries of the patient from the first and second sensors.

9. The method of claim 8, wherein the one or more carotid arteries comprises a left common carotid artery and a right common carotid artery.

10. The method of claim 1, wherein expanding the first expandable member comprises causing the first and second sensors to contact a trachea of the patient.

11. The method of claim 10, wherein obtaining data from at least the first and second sensors comprises obtaining data related to blood flow in an ascending aorta of the patient from the first and second sensors.

12. The method of claim 11, wherein the blood flow in the ascending aorta comprises blood exiting an aortic valve of the patient.

13. The method of claim 10, wherein the system further comprises a second expandable member carried by the elongate member distally of the first expandable member and configured to be expanded to contact a bronchus of the patient.

14. The method of claim 1, wherein expanding the first expandable member comprises causing the first and second sensors to contact an esophagus of the patient.

15. The method of claim 1, wherein each of the first and second sensors comprises an electrode.

16. The method of claim 1, wherein the system further comprises:
a processor configured to manipulate the data obtained by the first and second sensors and configured to calculate the stroke volume variation (SVV) of the patient.

17. The method of claim 1, wherein the first optical sensor is carried by the elongate member.

18. The method of claim 1, wherein the system further comprises:
a blood pressure cuff configured to be placed around a portion of the subject.

19. The method of claim 1, wherein the first and second sensors are each configured to output a signal indicative of impedance.

20. The method of claim 1, wherein the system further comprises:
a second optical sensor located at a second location in relation to the distal end of the elongate member, the second location different from the first location, wherein the system is further configured to calculate cardiac output of the patient utilizing data provided by the second optical sensor.

* * * * *